(12) United States Patent
Boulanger et al.

(10) Patent No.: US 6,420,120 B1
(45) Date of Patent: Jul. 16, 2002

(54) USE OF A POLYPEPTIDE AS CELL RECEPTOR FOR ADENOVIRUSES

(75) Inventors: Pierre Boulanger; Saw See Hong, both of Montpellier; Lucie Karayan, Poitiers, all of (FR)

(73) Assignee: Centre National de la Recherche Scientifique (CNRS), Paris Cedex (FR)

( * ) Notice: Subject to any disclaimer, the term of this patent is extended or adjusted under 35 U.S.C. 154(b) by 0 days.

(21) Appl. No.: 09/155,613

(22) PCT Filed: Jan. 30, 1998

(86) PCT No.: PCT/FR98/00184

§ 371 (c)(1),
(2), (4) Date: Sep. 30, 1998

(87) PCT Pub. No.: WO98/33929

PCT Pub. Date: Aug. 6, 1998

(30) Foreign Application Priority Data

Jan. 30, 1997 (FR) .............................. 97 01005
Sep. 9, 1997 (FR) .............................. 97 11166

(51) Int. Cl.⁷ ..................... G01N 33/53; G01N 33/567; C12N 15/63; C12N 15/85; C12N 15/86
(52) U.S. Cl. ..................... 435/7.1; 435/7.2; 435/320.1; 435/325
(58) Field of Search .......................... 435/7.1, 7.2, 325, 435/320.1; 514/44

(56) References Cited

U.S. PATENT DOCUMENTS 5,385,888 A 1/1995 Goodenow et al. ............ 514/12
6,054,281 A * 4/2000 Russell et al. ................ 435/7.1
6,057,155 A * 5/2000 Wickham et al. ............ 435/325

FOREIGN PATENT DOCUMENTS

WO 94 05303 3/1994
WO 95 05189 2/1995

OTHER PUBLICATIONS

Ding et al., A single Amino Acid Determines the Immunostimulatory Activity of Interleukin 10, 2000, J. Exp. Med., vol., 191 213–223.*

Verma, I.M. et al. Gene therapy–promises, problems and prospects, Nature, vol. 389, 1997, pp. 239–242.*

Orkin, S.H. Report and Recommendations of the Panel to asssess the NIH investment in research on gene therapy, Dec. 1995.*

Henry, L.J. et al, "Characterization of the knob domain of the denovirus type 5 fiber protein expressed in *Escherichia coli*", Journal of Virology, vol. 68, No. 8, Aug. 1994, ICAN Society for Microbiology US, pp. 5239–5246, XP002051921.

Hong, S.S. & Boulanger, P., "Protein ligands of the human adenovirus type 2 outer capsid identified by biopanning of a phage–displayed peptide library on separate domains of wild–type and mutant penton capsomers", EMBO Journal., vol. 14, No. 19, 1995, Eynsham, Oxford GB, pp. 4714–4727, XP002051922.

Chroboczek, J. et al, "Adenovirus fiber", Current Topics in Microbiology and Immunology, vol. 199, 1995, pp. 163–200, XP002051923.

Hong, J.S. & Engler, J.A., "Domains required for assembly of adenovirus type 2 fiber trimmers", Journal of Virology, vol. 70, No. 10, Oct. 1996, ICAN Society for Microbiology US, pp. 7071–7078, XP002052153.

Hong, S.S. et al, "Adenovirus type 5 fiber knob binds to MHC class I alpha 2 domain at the surface of the human epithelial and B lymphoblastoid cells", EMBO Journal, vol. 16, No. 9, May 1, 1997, Eynsham, Oxford GB, pp. 2294–2306, XP002051924.

* cited by examiner

*Primary Examiner*—Deborah J. R. Clark
*Assistant Examiner*—Eleanor Sorbello
(74) *Attorney, Agent, or Firm*—Burns, Doane, Swecker & Mathis, L.L.P.

(57) ABSTRACT

The subject of the present invention is the use of a polypeptide comprising at least 6 continuous amino acids of the sequence as shown in the sequence identifiers 1 to 5 as cellular receptor and/or coreceptor for adenoviruses. It also relates to the use of a cell capable of expressing such a polypeptide as well as that of a ligand capable of influencing the attachment of an adenovirus to a host cell and/or its entry into the said host cell. Finally, it also relates to a method for selecting or identifying a cellular receptor for a virus or the part of a viral protein which determines the attachment of the virus to its cellular receptor as well as to the use of a bifunctional ligand to target an adenovirus to a host cell carrying, at its surface, a surface protein other than the natural cellular receptor for the said adenovirus.

10 Claims, 8 Drawing Sheets

```
fiber:    ⁴³⁸V L A V K G S L A P I S G T V Q S A H L I I R F D E N G⁴⁶⁵
                                              (D)
106.3        V F - V K -- L - P
                   P - D V A P - S
                         L I P F N S
                               L S - N - Q S G
                                   S G V G Q A
                                     S V G D - Y G
                                     G - I -S - H T G
                                     G - I -S - H T G
                                     G - A -S - H T V
                                             H F Q Y R M
                                             R R I F R - D fiber:    ⁴⁷⁰N S F L D P E Y W N F R N G D L T⁴⁸⁶
                            (E)        (F)
7A2.7             M Q P V Y F
                L G P - V - N S
              A L - P - - H I V
              A - P - - H E L R
                M N V G A H
                V T S T Y H
                L Q K   V H - - R
                      D L W S V L
                        F W L A V R
                          W A L F R S
                          Y L G F F K
                              I A R - - L I S
                                R N Y T L T
                                R D A V M I
                              S R P T M L
```

FIG. 1

(a) mAB 7A2.7
```
R H R M L Q
  R R H - - W - P F
    W - Y E - W - I G
      W - V - I W S I
        I - L W T - P G
          L Q - Y S L P
        L - L D - F - - P A
              L T - P - N T I
              L G - K A - L P
                    S P H G S G
                    A P   M - V A L
                    T A A M - Y R
                          L F I A - R L
                          Y L Y G R V
                          A R V S R S
```

(b) Consensus sequence generated by competition with 7A2.7
    R H - I - L W T - P A N T P A M G Y L A - R V S Modules III of fibronectin
  FNIII$_1$: N S H P I Q - W N A P Q P S H I S K Y I L - R W R P K N
  FNIII$_4$: V K V T I - M W T P P E S A - V T G Y R V - D V I P V N
  FNIII$_5$: S T V L V R - W T P P R A Q - I T G Y R L - T V G L T R
  FNIII$_{14}$: N S L L V S - W Q P P R A R - I T G Y I I - K Y E K P S (c) mAB 106.3
```
A R A - I V G
      F V - W G L S
    F R V Q W - L
    Q V - H - L F R
      V Q W - F K P
        W - I - - F L M - Q
            R R Y F V - N
              Y F G S N S
            A Y G V M P
                L A P L G - K
          S R - L K M - G
              H M E L L M
              H S - - N G S R
                  T R - V R - T S
                    R - S E E T I
```

(d) Consensus sequence generated by competition with 106.3
    A R A - I V G F R V Q W - L R R Y F V - N G S R E T I α2 HLA domain (consensus):
  $^{156}$L R A Y L E G T C V E W - L R R Y L E - N G - K E T L Q$^{180}$

FIG. 2

USE OF A POLYPEPTIDE AS CELL RECEPTOR FOR ADENOVIRUSES

The subject of the present invention is the use of all or part of an antigen of the class I major histocompatibility complex and/or of a type III module of fibronectin to allow or facilitate the attachment of an adenovirus onto a host cell and/or its entry into the latter. The invention also relates to the use of a ligand capable of modulating the infectivity of an adenovirus toward a host cell, mediated by either of the polypeptides mentioned above. Finally, the invention relates to a biopanning method for identifying or selecting a cellular receptor for an adenovirus or one of these ligands, in particular of viral origin.

Adenoviruses are DNA viruses with a broad host spectrum. They have been detected in numerous animal species and can infect various cell types. Numerous serotypes have been characterized within each species which exhibit a genomic organization and an infectious cycle which are comparable. In general, the adenoviral genome consists of a double-stranded linear DNA molecule of about 36 kb containing the genes encoding the viral proteins and, at its ends, two inverted repeats (designated ITRs) which are involved in replication and the encapsidation region.

Adenoviruses replicate in the nuclei of the cells infected. The infectious cycle occurs in two stages. The early phase precedes the initiation of replication and makes it possible to produce the early proteins regulating the replication and the transcription of the viral DNA. These stages are followed by the late phase during which the structural proteins which constitute the viral particles are synthesized. The assembling of the new virions takes place in the nucleus. In the first instance, the viral proteins assemble so as to form empty capsids having an icosahedral structure, into which the adenoviral DNA is encapsidated. The viral particles are released and are capable of infecting other permissive cells. In this regard, the fiber and the penton base which are present at the surface of the capsids play a critical role in the cellular attachment of the virions and their internalization.

The adenovirus binds to the surface of permissive cells through the intermediacy of the trimeric fiber and a cellular receptor which has so far not been identified. Next, the particle is internalized by endocytosis through the binding of the penton base to the cellular integrins $\alpha_v\beta_3$ and $\alpha_v\beta_5$ (Belin and Boulanger, 1993, J. Gen. Virol. 74, 1485–1497; Mathias et al., 1994, J. Virol. 68, 6811–6814; Nemerow et al., 1994, Trends Cell. Biol. 4, 52–55; Wickham et al., 1993, Cell 73, 309–319; Wickham et al., 1994, J. Cell Biol. 127, 257–264). The Ad2 fiber comprises 580 amino acids (aa) whose sequence is disclosed in Herissé et al. (1981, Nucleic Acid Res. 9, 4023–4042). That of Ad5 has 582 amino acids (Chroboczek and Jacrot, 1987, Virology 161, 549–554). Its molecular mass is 62 kDa, but the native fiber behaves like a 160–180 kDa molecule, confirming its assembly in the form of a trimer.

The fiber is composed of 3 domains (Chroboczek et al., 1995, Current Top. Microbiol. Immunol. 199, 165–200):

(1) At the N-terminus, the "tail", which is highly conserved from one serotype to another, interacts with the penton base and ensures the anchorage of the molecule in the capsid.

(2) The "stem" is a structure in the form of a rod of variable length depending on the serotypes. For example, the stem of the Ad5 fiber contains 22 repeats of a motif of 15 residues which could adopt a β sheet conformation. The number of these repeats differs from one serotype to another, which explains the variations in length.

(3) Finally, at the distal end of the stem, the "head" or terminal sphericle is a globular structure containing trimerization signals (Hong and Engler, 1996, J. Virol. 70, 7071–7078; Novelli and Boulanger, 1991, J. Biol. Chem. 266, 9299–9303; Novelli and Boulanger, 1991, Virology 185, 365–376). Most of the experimental data show that it is the head domain which is responsible for the binding to permissive cells (Krasnykh et al., 1996, J. Virol. 70, 6839–6846).

(4) The complexity of the adenoviral attachment suggests that it could be serotype-dependent and that several cellular proteins could participate in it. As regards Ad2, Hong and Boulanger (1995, EMBO J. 14, 4714–4727) have identified a number of peptide motifs found in several cellular surface proteins which are capable of interacting with the capsid proteins (penton base and fiber), in particular the type III 5 and 14 modules of human fibronectin. The authers proceeded by immobilizing, on an inert support, penton base or fiber (ligand) with which they reacted a library of phages expressing random hexapeptides (designated phagotopes). The phages adsorbed, which in theory express phagotopes interacting with a motif carried by the adenoviral protein, are then eluted either conventionally at acidic pH or by competition with the other nonimmobilized capsid partner (eluent). However, the cellular receptor for adenoviruses and the region of the head precisely involved in the binding to the receptor have so far not yet been clearly identified.

A new technique of "biopanning" has now been carried out in which the immobilized ligand consists of the head domain of the Ad5 fiber and the eluent consists of a neutralizing antibody directed against the latter and two classes of phagotopes isolated depending on the antibody used. The first corresponds to a conserved sequence within the α-2 domain of the antigens of the class I major histocompatibility complex (α-2 MHC-I) and the second to a sequence found in the III modules of human fibronectin (FNIII). The data presented in the examples which follow support the hypothesis that the α-2 MHC-I constitutes the primary receptor for the serotype C adenoviruses and confirm the participation of the FNIIIs as coreceptor or cofactor. The regions of these two receptors and of the fiber which interact with each other have also been identified. In addition, an antagonist peptide has been generated which reproduces the motif of the α-2 MHC-I domain which neutralizes the attachment of adenoviruses and an agonist peptide reproducing the FNIII motifs which stimulates attachment.

Accordingly, the subject of the present invention is the use of a polypeptide comprising an amino acid sequence homologous or identical to at least 6 continuous amino acids of the sequence as shown:

(a) in SEQ ID NO: 1 starting with the leucine residue at position 1 and ending with the glutamine residue at position 25, (b) in SEQ ID NO: 2 starting with the asparagine residue at position 1 and ending with the asparagine residue at position 26, (c) in SEQ ID NO: 3 starting with the valine residue at position 1 and ending with the asparagine residue at position 25, (d) in SEQ ID NO: 4 starting with the serine residue at position 1 and ending with the arginine residue at position 25, and/or (e) in SEQ ID NO: 5 starting with the asparagine residue at position 1 and ending with the serine residue at position 25; to allow or facilitate the attachment of an adenovirus to a host cell and/or the entry of the said adenovirus into the said host cell.

For the purposes of the present invention, "polypeptide" is understood to mean any molecule consisting of a succession of at least 6, and preferably of at least 8, amino acids. The term polypeptide comprises both peptide molecules of short length (from 6 to a few tens of residues) and molecules which are longer (up to several hundreds of residues), provided, however, the envisaged use is allowed. It is specified that a polypeptide in use within the framework of the present invention may be derived from a native polypeptide as found in nature, in particular in humans, or a portion thereof. It may also be a chimera and comprise additional residues of any origin fused at the N- and/or C-terminus and/or inserted so as to form an open reading frame. It is also possible to use a mutant obtained by mutation, deletion, insertion and/or substitution of one or more amino acids relative to the sequences disclosed in the sequence identifiers (SEQ ID).

A preferred polypeptide within the framework of the present invention comprises, in addition, appropriate elements to ensure its anchorage in a cell membrane or its presentation at the surface of a cell. Such elements are known to persons skilled in the art. As a guide, there may be mentioned the presence of a signal peptide generally associated at the N-terminal position and of a transmembrane region exhibiting a high degree of hydrophobicity. However, use may also be made of other techniques, for example chemical techniques, to anchor or bind a polypeptide to a membrane or a cell surface.

"Homologous amino acid sequence" is understood to mean a sequence having a degree of homology of at least 70%, advantageously of at least 80%, preferably of at least 90% with at least 6 continuous amino acids of one of the sequences mentioned. The term identical refers to 100% homology. Persons skilled in the art know the general rules which make it possible to calculate the degree of homology between two sequences. The procedure is generally carried out by aligning sequences possibly with the aid of specialist computer programs. It may be necessary to artificially introduce vacant positions. Once the optimum alignment has been achieved, the degree of homology is established by counting all the positions in which the amino acids of the two sequences are found to be identical, relative to the total number of positions.

"Attachment of an adenovirus to a host cell" is understood to mean the binding of the viral particle to the cell. "Entry of an adenovirus into a host cell" denotes the penetration of the virus into the host cell. The attachment and/or the entry are preferably mediated, at least in part, by the polypeptide (s) in use within the framework of the present invention by interaction with the adenoviral capsid. Of course other polypeptide or nonpolypeptide molecules may also participate in these processes which are recognized in the art to be complex and multifactorial. They can be evaluated by any prior art technique, such as those described below using a permissive cell line and particles which are radio-actively labeled or which express a reporter gene, for example the luciferase gene. At 0° C., only the attachment can take place, the viral penetration requiring a temperature of 37° C.

For the purposes of the present invention, an adenovirus may be of human or animal (canine, avian, bovine and the like) or hybrid origin comprising genome fragments. These viruses and their genome are described in the literature (see for example Graham and Prevec, Methods in Molecular Biology, Vol. 7; Gene Transfer and Expression Protocols; Ed: E. J. Murray, 1991, The Human Press Inc., Clinton, N.J.). A replication-defective recombinant adenovirus expressing in particular a gene of therapeutic interest is preferred. Advantageously, the adenoviral genome is modified by deletion or mutation of sequences essential for replication and, in particular, contained in the E1, E2, E4 and/or L1–L5 regions (see for example international application WO 94/28152).

According to a first variant, the subject of the present invention is the use of a polypeptide comprising an amino acid sequence homologous or identical to at least 6 continuous amino acids of the sequence as shown in SEQ ID NO: 1 starting with the leucine residue at position 1 and ending with the glutamine residue at position 25.

Advantageously, a polypeptide in use within the framework of the present invention comprises an amino acid sequence homologous or identical to all or part of an antigen of the class I major histocompatibility complex (MHC-I) and, preferably, of the heavy chain of the latter.

All the cells of an organism have on their membrane molecules called histocompatibility antigens which define each individual. The corresponding genes, more than about ten, are located on chromosome 6 in humans and exhibit high polymorphism, which makes it possible to ensure a high variability of these identity markers. There are two different categories of these histocompatibility antigens, classes I and II respectively, whose structure and functions are distinct. The class I molecules, called HLA (for Human Leukocyte Antigen), are involved in presenting antigenic peptides at the cell surface and play an essential role in the antiviral immune responses exerted by the cytotoxic T lymphocytes.

The MHC-I molecules are heterodimers composed of a non-MHC light chain designated β2-microglobulin (β2m) and a heavy chain encoded by the MHC genes, which are noncovalently linked. The heavy chain is a membrane protein whose N-terminal part is oriented outside the cell whereas the C-terminal portion is cytoplasmic. The former comprises 3 domains designated α1, α2 and α3 having about 90 amino acids in each. It is followed by a transmembrane region of about 25 amino acids and then the C-terminal region of about thirty amino acids. Most of the variations between the products of the different alleles are located in the α1 and α2 domains, the α3 domain being relatively conserved and β2m being invariable (for a review and the sequence comparison between the members of the MHC-Is, see Bjorkman and Parham, 1990, Annu. Rev. Biochem. 59, 253–288).

Among the polypeptides suitable for the purposes of the present invention, there may be mentioned more particularly the HLA A, B, C, D, E and F antigens or polypeptides derived therefrom.

In a particularly advantageous manner, the polypeptide in use within the framework of the present invention comprises a sequence homologous or identical to all or part of the C-terminal region of the α2 domain of the MHC-I heavy chain and, more particularly, to the part centered on the tryptophan residue at position 167, in particular that extending from residues 156 to 180 (SEQ ID NO: 1). The numbering to which reference is made is in accordance with that used, for example, in Bjorkman and Parham (1990, supra).

According to another variant, a polypeptide in use within the framework of the present invention comprises an amino acid sequence homologous or identical to at least 6 continuous amino acids of the sequence as shown.

in SEQ ID NO: 2 starting with the asparagine residue at position 1 and ending with the asparagine residue at position 26, in SEQ ID NO: 3 starting with the valine residue at position 1 and ending with the asparagine residue at position 25, in SEQ ID NO: 4 starting with the serine residue at position 1 and ending with the arginine residue at position 25, and/or in SEQ ID NO: 5 starting with the asparagine residue at position 1 and ending with the serine residue at position 25.

A preferred polypeptide comprises an amino acid sequence homologous or identical to fibronectin and, in particular, to at least one of its type III modules and, in particular, to modules FNIII 1, 4, 5 and/or 14. Of course, it may comprise several of them. It is also possible to envisage using human fibronectin or a peptide derived therefrom, for example, by mutation or fragmentation. As a guide, the fibronectin encoded by a single gene is a molecule which is involved in adhesion and cell contact phenomena. Its sequence and its characteristics are described in the literature accessible to persons skilled in the art (see in particular Bork and Doolittle, 1992, Proc. Natl. Acad. Sci. USA 89, 8990–8994 and Dickinson et al., 1994, 236, 1079–1092). It is composed of 14 so-called type III modules (numbered from 1 to 14) whose primary sequence may vary, but whose β-sheet conformation is conserved.

According to a particularly advantageous embodiment, a polypeptide as defined above is more particularly intended to allow or to facilitate the attachment of a serotype C adenovirus to a host cell and/or its entry into the latter. Among the adenoviruses which may be envisaged, there may be mentioned more particularly serotypes 2 and 5.

The present invention also relates to a host cell capable of expressing a polypeptide in use within the framework of the present invention and its use to allow or to facilitate the attachment of an adenovirus to its surface and/or the entry of the said adenovirus. Various types of host cells may be considered. They may be cells of any origin, for example of microorganisms, yeasts, insects, plants or animals. A mammalian cell and, in particular, a human cell of the primary or tumor type or derived from a line which can be cultured in vitro will be preferred in particular. It may be of a hematopoietic (totipotent stem cell, leukocyte, lymphocyte, monocyte, macrophage and the like), hepatic or renal origin, from the central nervous system, fibroblast, epithelial, pulmonary or muscular (myocyte, myoblast, satellite cell, cardiomyocyte and the like) origin. A particularly preferred cell is or is derived from the 293 line established from embryonic kidney cells by integration of the adenoviral E1 region (Graham et al., 1977, J. Gen. Virol. 36, 59–72). It is indicated that the expression of one or more polypeptides in use within the framework of the present invention at the surface of a host cell not usually expressing the MHC-Is and/or fibronectin should allow its infectivity by an adenovirus. It could be used as a new cell producing adenoviral vectors. It is also possible to envisage the case of an overexpression in a cell naturally expressing the said polypeptide. An overexpressing line derived from the 293 line should make it possible to improve the yields of production of an adenovirus of interest. Of course, the polypeptide in use within the framework of the present invention may be associated with the cell by chemical means or by means of a ligand recognizing a cell surface protein. However, it is also possible to envisage expression by recombinant DNA techniques. Such an embodiment is within the capability of persons skilled in the art. As a guide, the nucleotide sequence encoding the polypeptide in question may be isolated (by standard PCR or cloning techniques) or chemically synthesized before being inserted into a conventional expression vector under the control of appropriate regulatory elements, the vector being introduced into the host cell by any prior art technique. The host cell in use within the framework of the present invention may also be modified so as to complement a defective adenovirus by transfection of (an) appropriate fragment(s) of adenoviral genome.

The subject of the present invention is also the use of a ligand capable of influencing the attachment of an adenovirus to a host cell and/or its entry into the latter, which are mediated by a polypeptide as defined above. The ligand in use in the invention may be of any type. There may be mentioned, for example, the peptides, hormones, antibodies or derivatives thereof and, in particular, single-chain antibodies of the scFv (for single chain fragment variable) type and soluble receptors lacking their transmembrane region. In particular, such a ligand may be derived from a polypeptide in use in the present invention. In accordance with the aims pursued by the present invention, the ligand may have a negative (antagonist) or positive (agonist) influence. Preferably, a preferred ligand has a dissociation constant with respect to the adenovirus of between 0.01 and 100 nM, advantageously between 0.1 and 50 nM, and most preferably between 0.5 and 10 nM.

In the case of an antagonist, the interaction of the ligand with the fiber will make it possible to reduce or inhibit the process of attachment and/or of entry of an adenovirus. In this context, a particularly preferred ligand is based on a polypeptide as defined in SEQ ID NO: 1. By way of example, there may be mentioned a polypeptide comprising an amino acid sequence homologous or identical to at least 6 continuous amino acids contained in the sequence as shown in SEQ ID NO: 6 starting with the arginine residue at position 1 and ending with the arginine residue at position 20. The use of the peptide designated MH20 in the examples which follow will be preferred.

In the case of a positive influence, the ligand in use within the framework of the present invention is used to allow or to stimulate the attachment and/or the entry of adenoviruses. A ligand which is suitable for the purposes of the invention comprises an amino acid sequence homologous or identical to at least 6 continuous amino acids of the sequence as shown in SEQ ID NO: 7 starting with the arginine residue at position 1 and ending with the serine residue at position 20. A preferred example consists of the peptide designated below FN20.

The present invention also relates to a ligand comprising an amino acid sequence homogous or identical to at least 6 continuous amino acids of the sequence as shown in SEQ ID NO: 6 or 7.

However, it may also be a ligand of adenoviral origin. According to this embodiment, a preferred ligand is derived from the fiber of an adenovirus, in particular from the part of the head which interacts with the abovementioned polypeptides. A peptide motif chosen in this region therefore ought to influence the infectivity of the adenoviruses with respect to a host cell expressing the polypeptide. Advantageously, a ligand covering residues 438 to 486 of the fiber of an adenovirus is used. More particularly, a ligand of a polypeptide as defined by SEQ ID NO: 1 is preferably derived from an Ad5 and comprises an amino acid sequence homologous or identical to at least 6 continuous amino acids of the sequence as shown in SEQ ID NO: 8, starting at the amino acid leucine at position 1 and ending at the amino acid aspartic acid at position 18. A ligand which may also be envisaged may be derived from the fiber of a serotype 2 adenovirus and may comprise an amino acid sequence homologous or identical to at least 6 amino acids of the sequence as shown in SEQ ID NO: 9 starting at the threonine residue at position 1 and ending at the valine residue at position 16.

The ligand of a polypeptide as defined by SEQ ID NO: 2 to 5 is more particularly characterized by an amino acid sequence homologous or identical to at least 6 amino acids of the sequence as shown in SEQ ID NO: 10 starting at the leucine residue at position 1 and ending at the threonine residue at position 14 (Ad5) or in SEQ ID NO: 11 starting at the asparagine residue at position 1 and ending at the asparagine residue at position 13 (Ad2).

The subject of the present invention is also the use of a ligand according to the invention for the preparation of a medicament intended to inhibit or reduce an infection by an adenovirus. In this context, the use of an antagonist ligand with a therapeutic or prophylactic objective will be preferred. The use of a ligand according to the invention, preferably an agonist ligand, is appropriate for the preparation of a medicament intended to promote or facilitate an infection by an adenovirus, and in particular a recombinant adenovirus carrying a therapeutic gene intended for gene (curative) or anti-viral (AIDS) or anti-cancer therapy. Such a medicament finds it usefulness, for example, in association with gene therapy treatments so as to improve viral infection in a patient treated with a recombinant adenovirus. It is possible to envisage a parenteral or oral administration or alternatively administration by aerosol. The administration may be made in a single dose or a dose repeated once or several times after a certain period of time. The appropriate dosage and formulation vary according to different parameters, for example the individual, the disease to be treated, the desired effect, the route of administration or alternatively the adenovirus in question.

The present invention also relates to a method for selecting or identifying a cellular receptor for a virus in an appropriate sample, comprising:
 (a) the immobilization, onto an inert support, of a reagent of viral origin comprising all or part of a surface protein of the said virus which determines its attachment to the cellular receptor,
 (b) the incubation with the sample for a determined time,
 (c) the elution of the sample retained in step (b) with all or part of an antibody directed against the said reagent of viral origin, and
 (d) the analysis of the sample eluted in step (c).

The inert support may be, without limitation, in any form (cone, tube, well, beads and the like) and may be made of any material (natural, synthetic, such as polymers, chemically modified or otherwise and the like). The attachment of the reagent to the inert support may be carried out in a direct or indirect manner. In a direct manner, the procedure will be preferably carried out by adsorption, that is to say noncovalently, although the establishment of covalent bonds may also be considered. In an indirect manner, an anti-reagent compound capable of interacting with the reagent may be attached beforehand so as to immobilize the whole onto the inert support. According to an advantageous embodiment, the sample consists of a so-called random library, and in particular an expression library (genomic fragments, cDNA) or a peptide library or, preferably, a phage library expressing peptide motifs (phagotopes). Such libraries are described in the literature or are commercially accessible. With the aim of selecting or identifying a cellular receptor for an adenovirus, there is preferably used as reagent of viral origin all or part of the fiber and, in particular, of the head of an adenovirus and, as eluent, an anti-fiber neutralizing antibody (inhibitor of the attachment of the virus to the surface of the host cell). The fiber or its fragments may be produced by the recombinant route and the antibodies by the hybridoma technique or by genetic engineering (production of single chain antibody scFv, Fab and the like). It is indicated that most anti-fiber antibodies are neutralizing. The analysis is carried out by comparing the sequence of the eluted sample with data banks. Such an analysis is within the capability of persons skilled in the art.

Finally, the present invention also relates to a method for selecting or identifying the part of a viral protein which determines the attachment of a virus to a cellular receptor in an appropriate sample, comprising:
 (a) the immobilization, onto an inert support, of all or part of an antibody directed against the said viral protein,
 (b) the incubation with the said sample for a determined time,
 (c) the elution of the sample retained in step (b) with a reagent of viral origin comprising all or part of the said viral protein, and
 (d) the analysis of the sample eluted in step (c).

The specific embodiments cited above may also apply in this context.

The subject of the present invention is also the use of a bifunctional ligand for targeting an adenovirus to a cell surface protein other than the natural cellular receptor for the said adenovirus, the said bifunctional ligand comprising a first ligand part capable of interacting with the fiber of the said adenovirus, a second ligand part capable of interacting with the said cell surface protein and, optionally, a spacer between the said first and second ligand parts.

For the purposes of the present invention, a bifunctional ligand is capable of interacting with two different species, one preferably situated at the surface of an adenovirus and the other at the surface of a host cell, at the level of a cell surface protein other than the natural cellular receptor for the said adenovirus. Moreover, the two ligand parts may be optionally separated by a spacer comprising from one to about fifteen amino acids which are preferably not charged. Of course, the order of the species is of no importance, it being possible for the domain interacting with the adenoviral protein to be at the N or at the C terminus of the bifunctional ligand, the C-terminal position being preferred. The use of such a bifunctional ligand makes it possible to target an adenovirus to a host cell of interest, for example a tumor cell, an infected cell, a particular cell type or a category of cells carrying a specific surface marker. After binding of the said bifunctional ligand to the cell surface protein, the species recognizing the adenoviral protein is exposed, which should create "lures" of viral receptors of the same type as the primary receptors ($\alpha 2$ domain of the MHC-Is) and create or increase the number of adenovirus primary receptors at the surface of the host cell.

Preferably, the ligand part interacting with the adenoviral fiber has the characteristics of the ligand defined above; it is in particular derived from the $\alpha 2$ domain of the MHC-I and preferably comprises an amino acid sequence homologous or identical to at least 6 continuous amino acids contained in SEQ ID NO: 6. Still more preferably, it consists of the peptide MH20 (SEQ ID NO: 6).

As regards the ligand part interacting with the cell surface protein, it is adapted to the host cell which it is desired to target. In the case of a cell infected by the HIV virus (Human Immunodeficiency Virus), the ligand may be an antibody fragment against fusin, the CD4 receptor or against an exposed viral protein (envelope glycoprotein) or alternatively the part of the TAT protein of the HIV virus extending from residues 37 to 72; (Fawell et al., 1994, Proc. Natl., Acad. Sci. USA 91, 664–668). In the case of a tumor cell, the choice will be for a ligand recognizing a tumor-specific antigen (MUC-1 in the case of breast cancer, antigens of the papillomavirus HPV and the like) or one which is overexpressed (IL-2 receptor overexpressed in certain lymphoid tumors). If it is desired to target the T lymphocytes, it is possible to use a T cell receptor ligand. Moreover, transferrin is a good candidate for hepatic targeting. There may also be mentioned the peptide EGF (abbreviation for Epidermal Growth Factor) which allows targeting to cells expressing the EGF receptor or the GRP peptide (for Gastrin Releasing Peptide) having the sequence (SEQ ID NO: 24) GNH-WAVGHLM (Michael et al., 1995, Gene Ther. 2, 660–668) which binds to the GRP cellular receptor. In general, the ligands which may be used in the context of the invention are widely described in the literature.

A bifunctional ligand in use within the framework of the present invention may be obtained by recombinant DNA techniques, by synthesis or by chemical coupling of the two parts of the ligands in question. Preferably, the adenovirus to be targeted is recombinant and carries a cytotoxic gene or is capable of inducing cellular apoptosis. Such genes are perfectly known. There may be mentioned, in particular, the gene encoding thymidine kinase of the HSV-1 virus (herpes simplex virus type 1).

By way of preferred examples, there may be mentioned a bifunctional ligand comprising the peptide MH20 and GRP. The MH20 and GRP peptide domains may be inversely oriented: respectively MH20-GRP when MH20 is at the N-terminal position and GRP-MH20 when MH20 is at the C-terminal position. Another embodiment uses a ligand having an MH20 species and an antibody species of the ScFv (Single Chain FV fragment) type. According to a particularly preferred embodiment, the said bifunctional ligand comprises an amino acid sequence homologous or identical to all or part of the sequence as shown:

(i) in SEQ ID NO: 22 starting at the arginine residue at position 1 and ending with the methionine residue at position 35, or (ii) (ii) in SEQ ID NO: 23 starting at the lysine residue at position 1 and ending with the arginine residue at position 35.

The present invention also relates to a bifunctional ligand as defined above and, in particular the ligands GRP-MH20 or MH20-GRP. The ligand GRP-MH20 is particularly preferred.

The subject of the present invention is also a cell carrying at its surface such a bifunctional ligand. The advantage of such a cell is to increase the number of primary receptors of the MHCI-α2 type. The said cell is advantageously a mammalian cell of any origin (see above). It is preferably a cell for complementation of an adenovirus defective for the E1 function and optionally for another function (E2, E4, E2 and E4, and the like, see Application WO94/28152). A preferred example is the 293 line. It may be generated by recombinant DNA techniques (expression of the bifunctional ligand by means of an appropriate vector comprising the elements allowing expression at the cell surface, for example signal sequence and/or transmembrane region), by covalent or noncovalent chemical bonding or by simple interaction between the cell and the ligand.

BRIEF DESCRIPTION OF DRAWINGS

The present invention is illustrated with reference to the following figures.

FIG. 1 (SEQ ID NOS: 35–61) presents the phagotopes obtained after biopanning using the antibody 1D6.3 (a) or 7A2.7 (b) as ligand. The peptide motifs of the phagotopes are aligned with respect to the sequence of the Ad5 head (the initiator methionine residue of the fiber representing +1. The regions forming the β sheet structures (Xia et al., 1994, supra) are underlined and indicated by (D), (E), and (F). The residues which are identical or conserved in the sequences are indicted in bold.

FIG. 2 (SEQ ID NOS: 62–98) presents the phagotopes obtained after biopanning using (a) the antibody 7A2.7 or (c) 1D6.3 as eluent, (b) and (d) the consensus sequences determined from the phagotopes (a) and (c) respectively as well as the homologous sequences found by analyzing the SWISS PROT data bank. The residues conserved at analogous positions are indicated in bold.

EXAMPLES

Figure 3A:
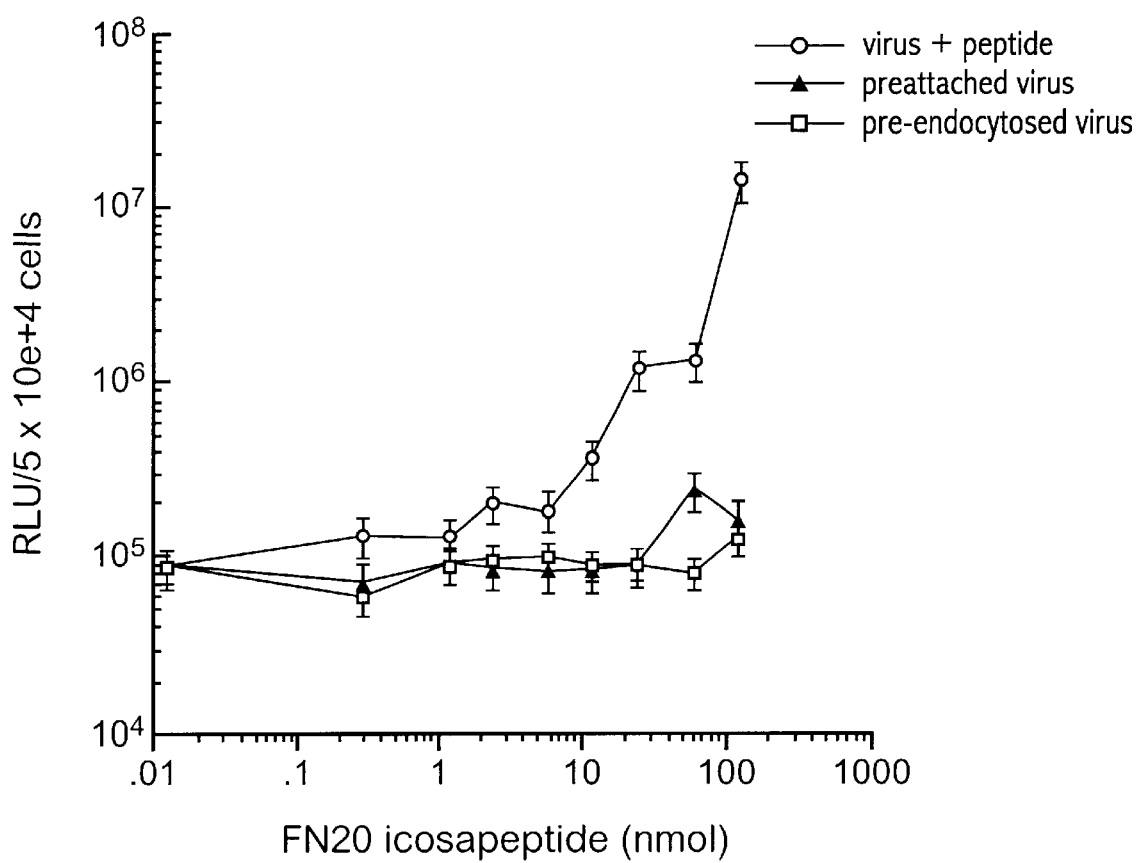
FIG. 3 (A–B) illustrates the expression of the luciferase gene in HeLa cells infected with the Ad5Luc3 virus at a constant MOI (0.16 pfu/$10^5$ cells). (○) the Ad5Luc3 is added to the cells cooled to 0° C. in the presence of increasing molarities of peptide (a) FN20 (0 to 500 μM or (b) MH20 (0 to 50 μM). The controls correspond to the incubation of the peptides after the attachment of Ad5Luc3 (Δ) or after endocytosis (□).

The HeLa cells (ATCC CCL2) are cultured in monolayers according to the prior art techniques. A DMEM medium (Dulbecco's Modified Eagle's Medium; Gibco) containing 10% heat-inactivated fetal calf serum (FCS), L-glutamine and the usual antibiotics, is preferably used. The Daudi HLA- (ATCC CCL213) and HLA+ (Quillet et al., 1988, J. Immunol. 141, 17–20) cells are maintained in RPMI 1640 medium (Gibco) supplemented with 15% FCS.

The wild-type Ad5 and the recombinant Ad5Luc3 are propagated between the HeLa cells by the standard techniques. As a guide, Ad5Luc3 is a replication-competent adenovirus which contains the luciferase gene placed under the control of the SV40 virus (simian virus 40) early promoter inserted into the E3 region of the adenoviral genome (Mittal et al., 1993, Virus Research 28, 67–90).

Example 1

Production of Monoclonal Antibodies (mAb) which is Capable of Inhibiting the Attachment of Ad5 to the Permissive Cells The murine mAbs 1D6.3 and 7A2.7 were generated by conventional techniques by injecting the head of the Ad5 fiber produced in bacteria by the recombinant route (Henry et al., 1994, J. Virol. 68, 5239–5246; Douglas et al., 1996, Nature Biotech 14, 1574–1578) into Balb/C mice. The fusion and the production of hybridoma clones are conventional techniques within the capability of persons skilled in the art. The secreting clones are selected by their recognition of the antigen which served for the immunization in ELISA. It is indicated that they exhibit a neutralizing activity toward the virions (Michael et al., in preparation).

Sero-reactivity of the Monoclonal Antibodies 1D6.3 and 7A2.7

The reactivity of the antibodies is tested with respect to the domain of the head of the fiber of 3 different serotypes (Ad2, Ad5 and Ad3) which is prepared by the recombinant route. The corresponding sequences are isolated by PCR (Polymerase Chain Reaction) from viral genomic DNA and then introduced into the AcNPV virus (*Autographa californica Nuclear Polyhedrosis Virus*) under the control of the polyhedrin promoter (Luckow and Summer, 1989, Virology 170, 31–39). The recombinant proteins are expressed in the Sf9 (*Spodoptera frugiperda*) insect cells. The general technology is detailed in Karayan et al. (1994, Virology 202, 782–796) and Novelli and Boulanger (1991, Virology 185, 365–376). More precisely, the Ad5 sequences carrying the last repeated motif of the stem followed by the head of the fiber are cloned with the aid of the primers represented in SEQ ID NO: 12 and 13. The sense primer corresponds to nucleotides 32164 to 32205 of the Ad5 genome (Chroboczek and Jacrot, 1987, Virology 161, 549–554), includes 4 mismatches so as to create a BamHI site and to replace the threonine at position 388 of the native fiber with an initiator ATG codon. The antisense primer corresponds to nucleotides 32919 to 32883 of the Ad5 genome and makes it possible to create a KpnI site in order to facilitate subsequent cloning steps. The recombinant protein harvested in the Sf9 cell supernatants is designated F5-AT386. The Ad2 head is produced from the baculovirus vector described in Louis et al. (1994, J. Virol. 68, 4104–4106). The expression product designated F2-AT388 starts at position 388 (by replacement of the Ala of the native sequence with a Met) and carries, in addition to the head domain, the last repeated motif of the stem. Finally, for the corresponding sequences of Ad3, a sense primer (SEQ ID NO: 14) is used which is designed to introduce an NcoI cloning site and to replace the Asn and Ser codons at position 124 and 125 with the Met and Ala codons respectively. The antisense primer (SEQ ID NO; 15) introduces a KpnI site. The expression product is designated F3-AT124.

The wells of an ELISA plate are coated with the recombinant protein F5-AT386, F2-AT388 or F3-AT124 with which the mAb 1D6.3 or 7A2.7 and then a labeled anti-mouse antibody (for example with phosphatase or peroxidase) are reacted. A positive reaction is observed toward the native recombinant protein F5-AT386. No reaction is detected in the wells containing the protein F5-AT386 denatured with SDS or in those containing the native or denatured products F2-AT388 and F3-AT124. These data suggest that these antibodies recognize a serotype C-specific conformational epitope.

Inhibitor Effect of the Monoclonal Antibodies 1d6.3 and 7A2. 7 on the Cellular Attachment of Ad5.

A test for microbinding onto HeLa cells in culture is carried out with the aid of Ad5 virions labeled with [$^{14}$C] valine (specific activity of 2200 to 2500 cpm/$10^8$ virions) followed by autoradiography in situ (Silver and Anderson, 1988, Virology 165, 377–387). To do this, the cells at the semiconfluent state are placed in the presence of a constant quantity of radioactive virions ($10^3$ cpm per $5\times10^4$ cells) at a multiplicity of infection (MOI) of 1000 virions per cell for 1 h at 0° C. in the presence of mAb 1D6.3 or 7A2.7 (1:10, 1:8, 1:4 and 1:2 dilutions of the respective hybridoma supernatants whose mAb concentration is estimated at 0.1–0.2 μg/ml, which corresponds to an excess of mAb relative to the virions present in the inoculum of 100, 250, 500 and 1000 respectively). The cells are then washed in the presence of PBS, fixed with 0.1% paraformaldehyde in PBS, dried and covered with the K4 emulsion in gel form (Ilford Nuclear Research). After an exposure of one week and developing (developing agent D19B, Kodak), the samples are briefly stained with 0.5% toluidine blue, taken up in $H_2O$ and examined under a microscope. The density of the reduced silver crystals around the contour of the cells is representative of the number of [$^{14}$C] virions bound to the cell surface.

In the absence of an anti-head mAb or at a low concentration (1:10 dilution), a dark halo of reduced silver crystals is visible around the cells, indicating adsorption of the virions to their surface. A reduction in the halo which is dependent on the mAb concentration is observed for the 1:8, 1:4 and 1:2 dilutions. These results reflect a blocking of the binding of the adenoviral head to the primary cellular receptor due to the 1D6.3 and 7A2.7 mAbs directed against this part of the fiber. Comparison of the surface area of the halos for the same dilutions shows that the 1D6.3 antibody is more inhibitory of the attachment of Ad5 to the HeLa cellular receptor than the mAb 7A2.7.

Example 2

Identification of the Epitopes for the mAb 1D6.3 and 7A2.7

The epitopes of the fiber being assumed to be conformational (Fender et al., 1995, Virology 214, 110–117), the conventional method of identification of epitopes by scanning of peptides is not appropriate. The procedure is carried out according to a biopanning technique derived from those described by Smith and Scott (1993, Methods Enzymol. 217, 228–257) and Hong and Boulanger (1995, EMBO J. 14, 4714–4727). In this case, the mAb 1D6.3 or 7A2.7 is adsorbed overnight at 4° C. onto a microtiter plate (Nunc Immunomodule MaxiSorp F8) at a concentration of 1 μg/well in a 0.1 M sodium carbonate buffer pH 9.6. The immobilized antibodies are brought into contact with a phage library expressing hexapeptides (fUSE5 phages; Scott and Smith, 1990, Science 249, 386–390). In a second step, the phages retained are eluted either with a conventional acidic elution buffer or, more selectively, by competition in the presence of an excess of recombinant protein F5-AT386. The hexa-peptide motifs (phagotopes) carried by the eluted phases are determined by sequencing the protein pIII fUSE5 by the method of Sanger et al. (1977, Proc. Natl. Acad. Sci. USA 74, 5463–5467). The sequence homologies with the phagotopes are searched out in the Swiss Prot data bank and the FASTA 1.6 program (Pearson and Lipman, 1988, Proc. Natl. Acad. Sci. USA 85, 2444–2448) and the sequence alignments made using version W(1;4) of the Clustal program (Higgins and Sharp, 1988, Gene 73, 237–244).

As shown in FIG. 1, the mAb 1D6.3 retains different phagotopes whose sequences overlap, and are homologous to the Ad5 head extending between the Val residue at position 438 and the Asp residue at position 462. In spite of a degree of degeneration and dispersion, it was possible to determine a central motif of sequence LAPISGTVQSAHLI-IRFD corresponding to the amino acids at positions 445 to 462 (SEQ ID NO: 8). This motif is centered on the His residue at position 456, which corroborates the presence of histidine in several independent phagotopes. Furthermore, three phagotopes (SEQ ID NOS: 25–27) contain a hisitidine close to a serine (GISHTG and GASHTV) and a homologous sequence is found in the head ($^{453}$QSAHLI$^{458}$). On the N-terminal side, the sequence (SEQ ID NO: 28) LAPIS is represented in several phagotopes (SEQ ID NOS 29–30) in the form L-P, VAP-S and LIPFNS.

The sequence analyses of the 15 phagotopes retained by the mAb 7A2.7 demonstrated the presence of a proline on 4 occasions, of tryptophan and histidine 8 times and the association in the same phagotope of two aromatic residues is found five times. It therefore seems that the epitope for the mAb 7A2.7 contains a proline residue, such as the one at position 475 of the fiber, near a group of aromatic residues, such as $^{477}$YWNF$^{480}$ (SEQ ID NO 31). In addition, two phagotopes (SEQ ID NOS: 32–33) FWLAVR and WALFRS are homologous to the motif $^{477}$YWNFR$^{481}$ (SEQ ID NO 34). On the basis of these data, the epitope for the mAb 7A2.7 was mapped between residues 473 and 486 of the Ad5 fiber (SEQ ID NO: 10).

In short, the mAbs 1D6.3 and 7A2.7 recognize adjacent segments of 15 to 20 aa in the linear sequence of the Ad5 head, the residues extending from positions 445 to 462 and 473 to 486 respectively. According to the three-dimensional model of the head proposed by Xia et al. (1994, Curr. Biol. Structure 2, 1259–1270), the two epitopes occupy regions which are continuous from a spatial point of view. The epitope for the mAb 1D6.3 covers part of the CD loop and of the β sheet D, whereas the epitope for the mAb 7A2.7 is located at the level of the adjacent segment DE and of the two β sheets E and F. The 1D6.3 epitope is situated inside a sheet R whereas the 7A2.7 epitope is oriented more sideways relative to the sheet R.

Example 3

Identification of the Cellular Receptors for Ad5 by the Reverse Biopanning Technique This technique is termed reverse relative to the preceding one since the fiber is used as ligand and the mAb as eluent. The procedure is therefore carried out by immobilizing the head of the Ad5 fiber with which the phage library expressing hexapeptide phagotopes is reacted. The phages adsorbed may be eluted either with a conventional acidic buffer or with the mAb 1D6.3 or 7A2.7 and the recombinant protein pIII carrying their respective phagotopes is sequenced. The search in data banks is carried out as above. The hexapeptide motifs identified are presented in FIG. 2.

The phagotopes produced by competition with the mAb 7A2.7 are presented in FIG. 2a. Their analysis makes it possible to derive a consensus sequence (FIG. 2b) which exhibits homology with the motifs 1, 3, 5 and 14 of the type III module of human fibronectin (SEQ ID NO: 2 to 5) (Main et al., 1992, Cell 71, 671–678). They are situated at the level of the β sheet B and of the adjacent BC loop of the FNIII module (Dickinson et al., 1994, J. Mol. Biol. 236, 1079–1092).

The phagotopes eluted after the action of the mAb 1D6.3 are described in FIG. 2c. All the sequences overlap and make it possible to also determine a consensus sequence (FIG. 2d). The search for homology with the sequences listed in data banks reveals homology with the C-terminal region of the α-2 domain of the heavy chain of the class I MHC molecules (MHC-1α-2) (position 156 to 180) (SEQ ID NO: 1).

Example 4

Interactions of the Adenoviral Fiber with the FNIII Model and the MHC-1α-2 Domain The interaction is studied in vitro with the aid of a chimeric protein derived from the C-terminal fusion of the GST (Glutathione S-transferase) protein to a pentadecapeptide RHILWTPANTPAMGY reproducing the consensus sequence homologous to the β sheet B and the BC loop of FNIII (see preceding example and FIG. 2b). To do this, the oligonucleotides presented in the sequence identifiers 16 and 17 are hybridized and introduced into the XhoI site of the plasmid pGEX-KG (Guan and Dixon, 1991, Anal. Biochem. 192, 262–267). It should be noted that the oligonucleotides, once rehybridized, generate an XhoI site at the 5' end if the insert is cloned in the correct orientation. This makes it possible to integrate a single copy or multiple copies in tandem at the level of the reconstituted XhoI site. The sequence of the fusion product comprising a copy of the pentadecapeptide (designated GST-FNx1) may be schematically represented in the following manner: GST– (site for cleavage by thrombin-PGIS-GGGGG-ILDSMGRLE-RHILWTPANTPAMGY(V)-ELKLNS-stop. The constructs GST-FNx2 and GST-FNx3 comprise respectively 2 and 3 repeats of the pentadecapeptide between residues LE and EL of the cloning cassette.

The sense and antisense oligonucleotides (SEQ ID NO: 18 and 19) encoding the consensus sequence obtained by competition with the mAb 1D6.3 (FIG. 2d) are inserted according to the same strategy as above at the C-terminal end of GST to give the constructs GST-MHCx1, GST-MHCx2 and GST-MHCx3 depending on the number of motifs present. The chimeric proteins GST-FN and GST-MHC are produced in E. coli, extracted and affinity purified on agarose-glutathione beads (Sigma) according to conventional methods (Smith and Johnson, 1988, Gene 67, 31–40).

In parallel, the complete fibers of serotypes 2, 3 and 5 are produced by the recombinant route according to the baculovirus/Sf9 cell technology already used. The construct F2-FL582 carrying the gene for the Ad2 fiber is described in Novelli and Boulanger (1991, Virology 185, 365–376). The sequences encoding the Ad5 and Ad3 fibers are isolated by PCR using the viral DNA as template and appropriate sense and antisense primers such as those listed in SEQ ID NO: 20 and 13 and 21 and 15. The amplified segment is introduced into a baculovirus vector under the control of the polyhedrin promoter and the expression product recovered in the culture supernatants. F5-FL581 and F3-FL320 corresponding to the Ad5 and Ad3 fibers respectively are obtained.

The capacity of the FNIII module and of the recombinant α-2 MHC-1 domain to bind the adenoviral fiber is evaluated by immunotransfer after in vitro incubation of the fusion proteins GST-FN and GST-MHC and of the recombinant fibers F2-FL582, F5-FL581 and F3-FL320. The complexes formed are isolated on agarose glutathione beads under the conditions described by Johnson et al. (1995, J. Biol. Chem. 270, 24352–24360) and then analyzed on 12.5% polyacrylamide gel (SDS-PAGE) using a discontinuous buffer system (Laemmli, 1970, Nature 227, 680–685). The proteins are transferred onto a nitrocellulose membrane (0.8 mA/cm$^2$; Cambridge Electrophoresis system, UK) in a 25 mM Tris-HCl, 192 mM glycine buffer, pH 8.3 containing 20% methanol. After treating with a blocking solution (5% skimmed milk, 1% calf serum in TBS-T buffer: 20 mM Tris-HCl pH 7.8, 0.15 M NaCl, 0.05% Tween 20), the membrane is brought into contact with the antibody 4D2.5

(Hong and Engler, 1991, Virology 185, 758–767) and then a horseradish peroxidase-labeled anti-IgG conjugate. The revealing by the chemiluminescent peroxidase substrate (SuperSignal, Pierce Chemicals) is carried out according to Carriére et al. (1995, J. Virol. 69, 2366–2377) and the luminograms (Hyperfilm β-max, Amersham) are analyzed at 610 nm with the aid of an automated densitometer (REP-EDC, Helena Laboratories, Beaumont, Tex.). As a guide, the antibody 4D2.5 recognizes the FNPVYP epitope of the tail domain conserved in most mammalian adenoviruses.

GST-FNx1, GST-FNx2 and GST-FNx3 bind to F5-AT386 and F2-AT388 with high efficiency whereas F3-AT124 is retained to a lesser extent. A similar behavior is observed with the chimeric proteins GST-MHCx1, GST-MHCx2 and GST-MHCx3 which retain F5-AT386 and F2-AT388 with a higher efficiency than F3-AT124.

The Ad5 fiber binds to the fusion proteins GST-FN and GST-MHC with an affinity two to three times greater compared with the Ad2 fiber and ten to fifteen times greater compared with the Ad3 fiber. Furthermore, the binding efficiency is not dependent on the number of motifs present in the fusion protein, the intensity being comparable and even sometimes lower between GST-FNx1 and GST-FNx3 and GST-MHCx1 and GST-MHCx3. This may be explained by the fact that the motifs in tandem may adopt a conformation which interferes with the binding.

Example 5

Influence of the Synthetic Peptides Derived from FNIII and MHC-1α2 on the Attachment of Viruses to the Cell Surface Two synthetic peptides reproducing the FNIII and MHC-Iα2 motifs were chemically synthesized and purified according to the prior art techniques. FN20 (SEQ ID NO: 7) reproduces the consensus sequence of the phagotopes eluted by the antibody 7A2.7 and MH20 (SEQ ID NO: 6) corresponds to that of the phagotopes eluted by the mAb 1D6.3.

The peptides FN20 and MH20 are tested with respect to the attachment of the reporter adenovirus Ad5Luc3 to HeLa cells cultured in vitro. The test is carried out in part at 0° C., a temperature which allows the attachment of the viruses to the surface of the permissive cells but, on the other hand, blocks the entry of the viruses and the recycling of the receptors. Ad5Luc3 (MOI 0.16 pfu/$10^5$ cells) is previously incubated with increasing quantities of peptides (0.01 to 500 nM) at room temperature for 2 hours and the mixture is then added to a cell culture placed on ice. After 1 h at 0° C., the nonadsorbed viruses and the peptides are removed by washing and the culture is continued for 18 h at 37° C. after adding a preheated medium. The cellular lysates are prepared in a conventional manner and the luciferase activity expressed in RLU (for Relative Light Units) is determined (Promega substrate, Madison, Wis.; Lumat LB-9501 luminometer, Brethold Bioanalytical, Wildbad, Germany).

The results of competition with the peptide FN20 are presented in FIG. 3a. No significant effect is obtained up to a molarity of 10 μM and then a gradual increase in the luciferase activity appears above 25 μM. In particular, the activity increases by a factor of 100 between 25 and 100 μM. The peptide FN20 therefore has a stimulatory effect on the viral attachment. It confers no apparent cytotoxicity and has no negative effect on the expression of the luciferase gene once the virus is preattached (peptide added to the cell culture after the step of viral attachment at 0° C.) or preendocytosed (peptide added to the cell culture after the step of attachment and of penetration of the virus).

Figure 3B:
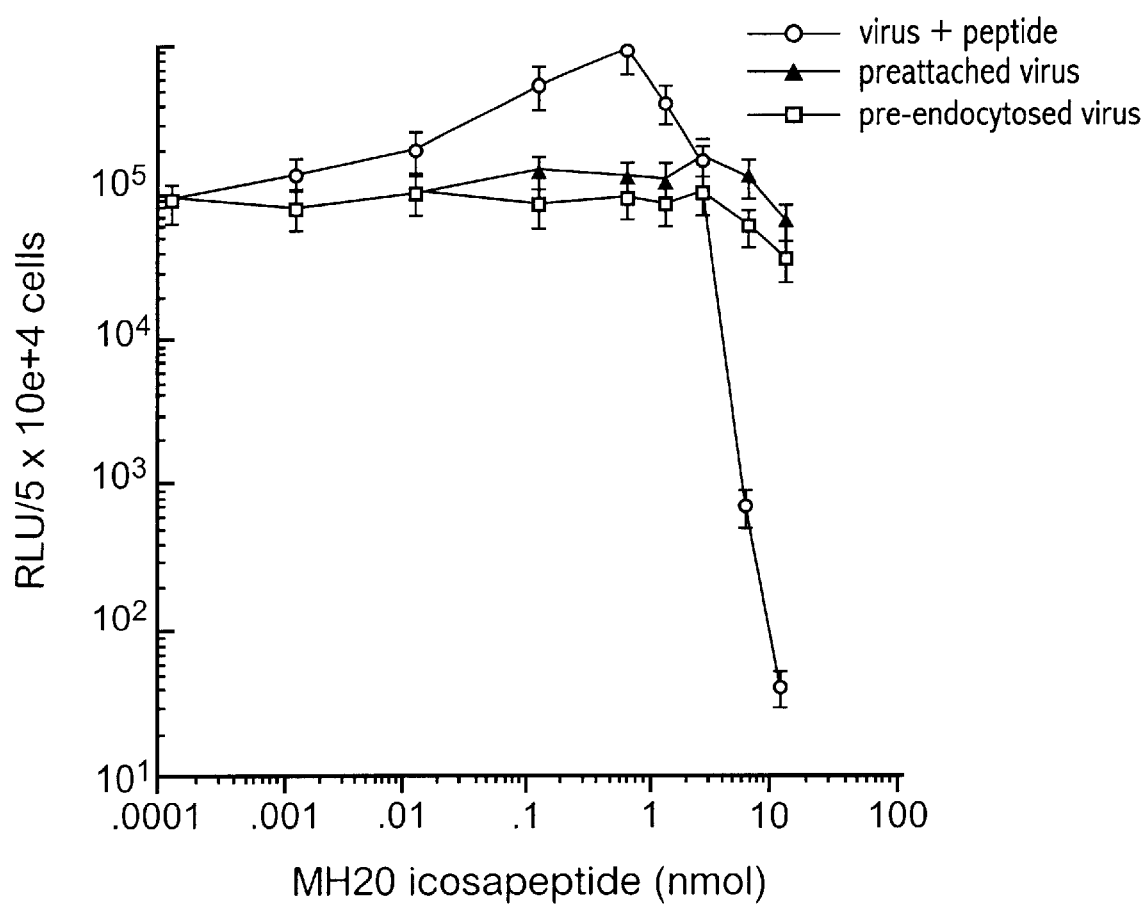

In the case of the peptide MH20 (FIG. 3b), a slight increase in the expression of the luciferase gene is observed for molarities of between 0.05 and 2.5 μM (activity five to six times greater at 2.5 μM). This phenomenon is followed by a rapid decrease in the luciferase levels when the molarities used are greater than 5 μM, with a decrease by a factor of 100 compared with the control at 25 μM and by almost four orders of magnitude at 50 μM, showing that bound to the virus, it blocks the attachment to the cell receptor. As above, the peptide MH20 at concentrations of 50 μM, exhibits no cytotoxic effect and does not influence the expression of the reporter gene after preattachment or preendocytosis of Ad5Luc3. The practically complete inhibition of the luciferase activity in the presence of 50 μM of MH20 is a reflection of complete neutralization of the virus.

Example 6

Sero-specificity of the Viral Neutralization by the Synthetic Peptides

The wild-type adenoviruses Ad5, Ad2 Ad3 are preincubated for 2 h at room temperature with the inhibitory peptide MH20 at a constant molarity (25 μM), the MOI varying from 0.2 to 2 pfu/cell. The mixture is placed in the presence of the HeLa cells for 1 h at 0° C. and the culture continued at 37° C. after removal of the nonadsorbed viruses under the same conditions as those described above. The level of synthesis of the hexon, of the 100 k protein, of the penton base is of the fiber is estimated by immunotitration (Wohlfart, 1988, J. Virol. 62, 2321–2328) on cellular extracts collected 48 h after infection.

The infection of the HeLa cells with Ad5 or Ad2 at an MOI of 0.2 to 2 pfu/cell in the presence of 25 μM of MH20 during the virus attachment phase is followed by inhibition of the synthesis of the proteins of the viral capsid hexon, 100 k protein, penton base and fiber 48 h after the infection (factor 15 to 30). On the other hand, when the infection is carried out under the same conditions with the wild-type Ad3, the synthesis of the structural proteins is only reduced by a factor of 1.5 to 2, which suggests that the adenoviral neutralization by MH20 is serotype-dependent.

Example 7

Affinity of the Ads Fiber for the Peptides FN20 and MH20

5, 10 and 25 μM of synthetic peptides FN20 or MH20 are immobilized on the polystyrene surface of a 96-well microtiter plate (Nunc, Maxisorb) overnight at 4° C. After washing and then blocking with a 3% solution of bovine serum albumin (BSA) in PBS buffer, increasing concentrations of F5-FL581 fibers taken up in PBS buffer and radioactively labeled (labeling with [$^{35}$S]methionine and [$^{35}$S] cysteine; specific activity of 50,000 to 65,000 cpm/μg of protein) are caused to react. The fiber adsorbed onto either of the peptides is eluted with a suitable solution (1 M urea, 1 M NaOH and 1% SDS) and then precipitated in the presence of trichloroacetic acid. The radioactivity content in the precipitate recovered on the GF/C filter is counted with the aid of a liquid scintillation spectrometer (Beckman LS-6500) and the dissociation constants (Kd) determined according to Scatchard (1949, Annls NY Acad. Sci. 51, 660–672).

The Kd of the labeled Ad5 fiber with respect to the peptide MH20 is evaluated at 3.0±0.6 nM and that found for the peptide FN20 is 8.0±1.9 nM (n=3 in both cases).

Example 8

The Infectivity of Ad5 is Dependent on the Expression of the MHC-I at the Surface of the Permissive Cells The Daudi line of B lymphoblastoids, which is established from a Burkitt's lymphoma, is naturally deficient in the expression of $\beta_2$-microglobulin and, as a result, does not possess at its surface class I HLA molecules (Daudi HLA−). The cell line E8.1 derived from the Daudi was generated by transfection of a gene encoding $\beta_2$-microglobulin so as to restore the expression of the class I HLA molecules at their surface (Daudi-HLA+; Quillet et al., 1988, J. Immunol. 141, 17–20).

Figure 4:
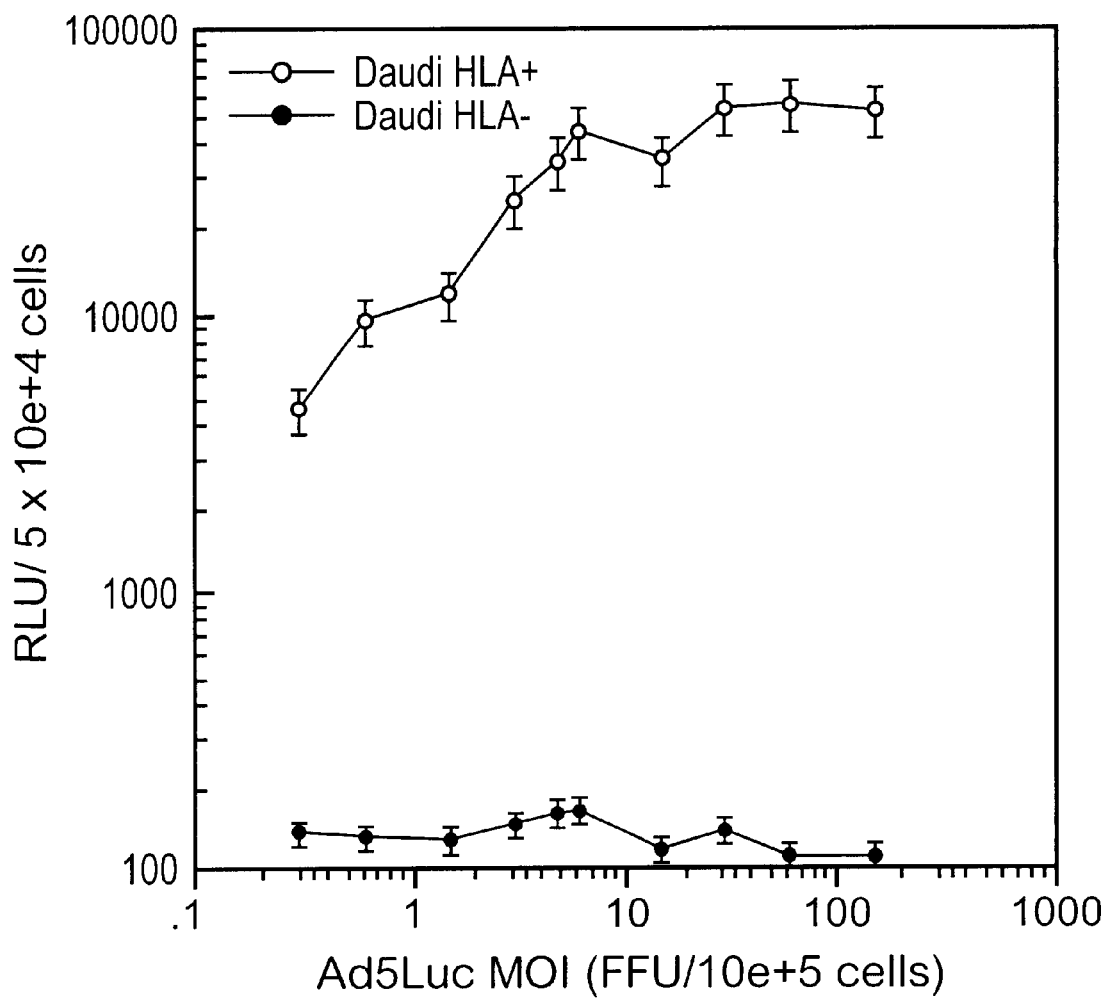
FIG. 4 illustrates the expression of the luciferase gene in Daudi-HLA- (○) or Daudi-HLA+ (○) cells infected with increasing concentrations of Ad5Luc3 (0.3 to 150 pfu/$10^5$ cells). The Ad5Luc3 is brought into contact with the cells precooled to 0° C. for 1 h in order to allow viral attachment but not the entry. The luciferase activity is evaluated after 18 h of culture at 37° C. The RLU values represent the mean of three separate experiments.

The experiments for attachment of Ad5Luc3 at 0° C. were carried out on Daudi HLA− and Daudi-HLA+ cells with an MOI of three orders of magnitude greater than that used in the case of HeLa cells (0.3 to 150 pfu/$10^5$ cells). The luciferase activity measured in the cellular lysates 18 h post-infection is represented in FIG. 4. When the infection relates to Daudi-HLA+ cells, the luciferase activity increases regularly in an MOI-dependent manner until a plateau is reached above 5 pfu/$10^5$ cells. As regards the Daudi HLA− cells, the luminescent signal is very low (3 to 4 orders of magnitude) compared to that observed with the cells provided with functional HLA molecules at their surface. These experiments show that the expression of MHC-I at the cell surface is necessary for the Ad5 infection.

Example 9

Bifunctional Ligand Mimicking the Primary Receptors for the Adenovirus

This example describes the construction of a bifunctional peptide which contains two domains, one recognizing the head of the adenoviral fiber and the other a cell surface protein. A peptide is used below in which MH20 is fused to GRP (Gastrin Releasing Peptide). Two constructions are possible, orienting the two peptide domains in a reversed manner, N-versus C-terminus, giving rise to the peptide MH20-GRP (SEQ ID No: 22) and to the peptide with the reverse orientation GRP-MH20 (SEQ ID No: 23).

Figure 5:
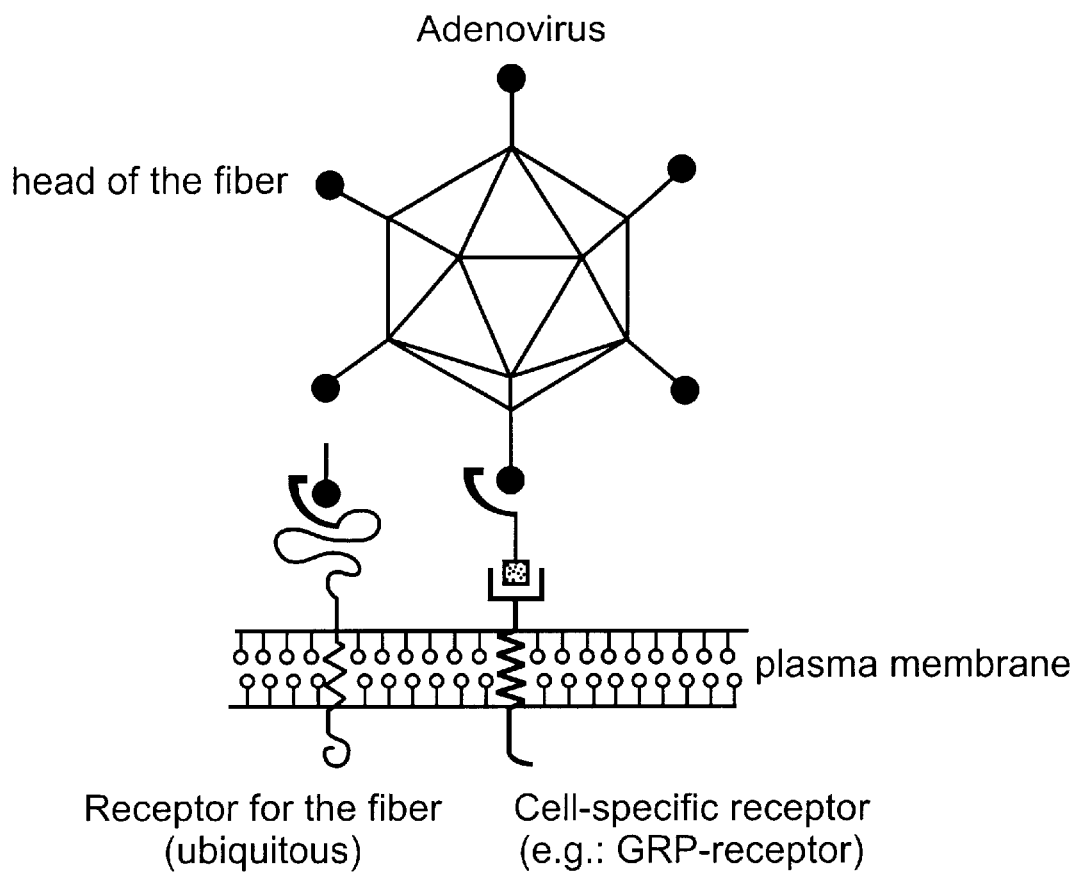
FIG. 5 illustrates the principle of the bifunctional ligand method mimicking the primary receptors for the adenovirus.

As illustrated in FIG. 5, the binding of this peptide to the cell surface GRP receptors should create "lures" of viral receptors of the same type as the primary receptors, that is to say the $\alpha$2 domain of the MHC class I molecules. The apparent result is to create or to increase the number of primary viral receptors for the adenovirus at the surface of cells possessing GRP receptors.

The human cells (HeLa) or murine cells (Swiss-3T3 or NIH-3T3, ATCC CRL-1658) are rinsed and incubated between 0 and 4° C. with an isotonic solution (PBS) containing 500 $\mu$M of peptide. After 1 h, the solution is removed and replaced with the viral inoculum (Ad5Luc3) according to a protocol already described (see above or Hong et al., 1997, EMBO J. 16, 2294–2306). The virus is incubated for 1 hour between 0 and 4° C. to allow its attachment, and then the excess nonadsorbed virus is rinsed with culture medium precooled to 4° C. and the cells are again placed at 37° C. in the presence of culture medium preheated to 37° C. The virus is endocytosed at 37° C. and the viral cycle then lasts for 18 to 20 h at 37° C.

Figure 6A:
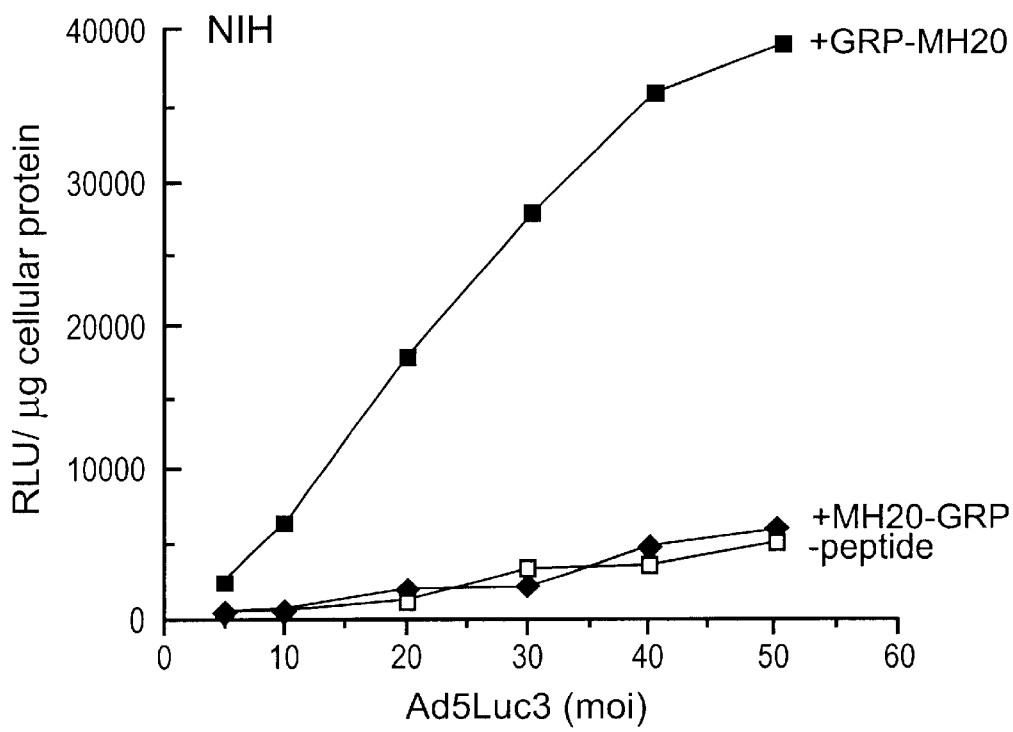
FIG. 6 (A–C) represents the luciferase enzymatic activity as a function of the MOI of Ad5Luc3 on NIH cells (a), Swiss 3T3 cells (b) and HeLa cells (c).
Figure 6B:
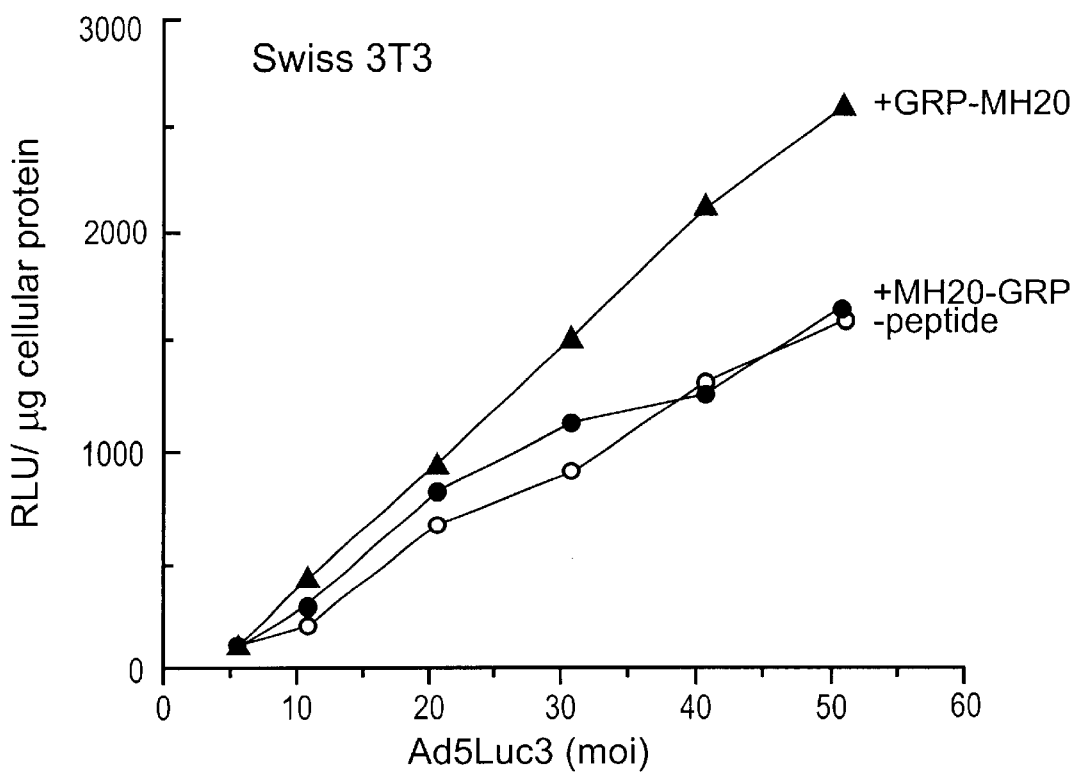
Figure 6C:
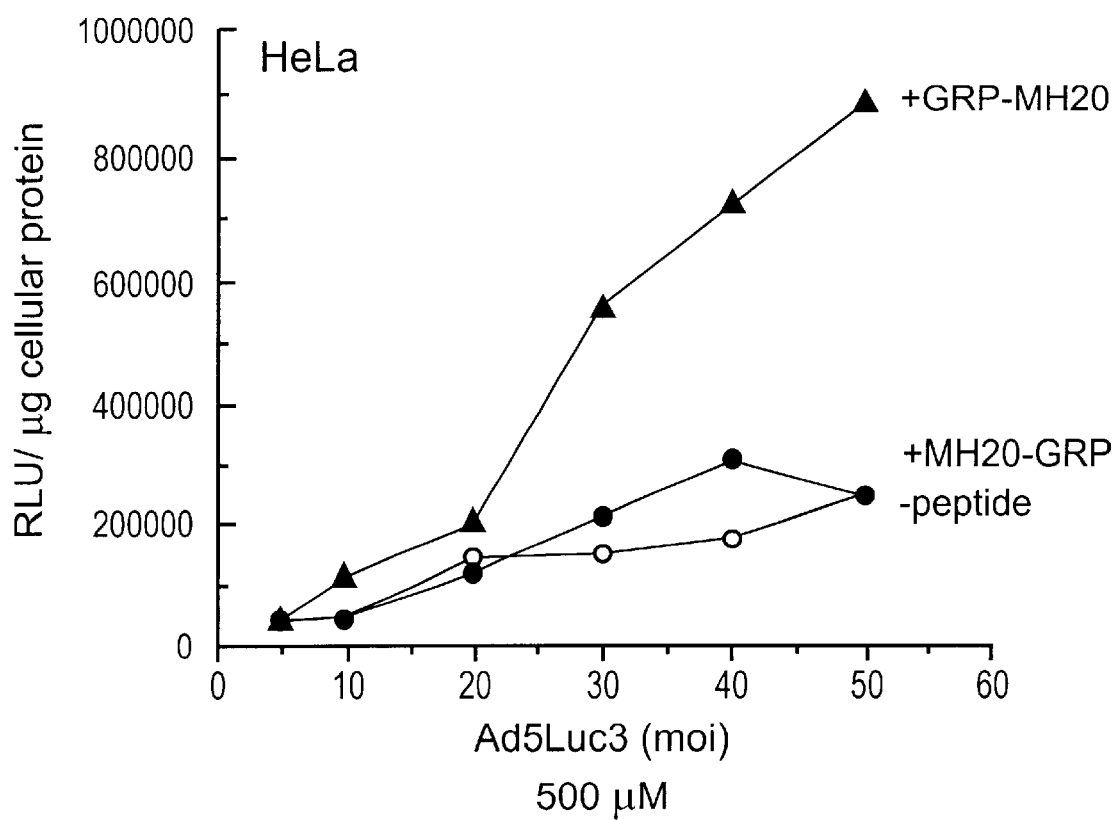

As shown in FIG. 6, it is observed that the curves obtained in the absence of any peptide (control curves indicated:-peptide) and those in the presence of peptide in the MH20 orientation N-terminus side—bound to GRP at the C-terminus (MH20-GRP) have an identical slope.

On the other hand, in the case of the reverse orientation, GRP on the N-terminus side, and MH20 on the C-terminus side, the increase in the number of adsorbed viruses is significant, as shown by the increase in the luciferase activity: eight to ten times for NIH-3T3, five to six times for the HeLa cells and two to three times for the Swiss-3T3. The binding of the GRP portion of the bifunctional peptide, ligand for the GRP receptors, made it possible to increase the apparent number of receptors for the Ad5 fiber of the alpha 2 domain type of the MHC class I molecules (MHC I-$\alpha$2).

What is claimed is:

1. A method for reducing or inhibiting the attachment of an adenovirus to a host cell in vitro or the entry of said adenovirus into said host cell, wherein said method comprises any one of the following steps
   (i) contacting said adenovirus with a ligand which is effective to reduce or inhibit said attachment or entry before infecting said host cell; or
   (ii) infecting said host cell by said adenovirus in the presence of said ligand; or
   (iii) contacting said host cell with said ligand and infecting with said adenovirus;
wherein said ligand comprises the amino acid sequence shown in SEQ ID NO: 6.

2. The method of claim 1, wherein said ligand consists of the amino acid sequence as shown in SEQ ID NO: 6.

3. The method of claim 1, wherein said ligand has a dissociation constant (kd) with respect to said adenovirus of 0.01 to 100 nM.

4. The method according to claim 1, wherein said adenovirus is of serotype C.

5. The method according to claim 4, wherein said adenovirus is of serotype 2 or 5.

6. A method for promoting or facilitating the attachment of an adenovirus to a host cell in vitro or the entry of said adenovirus into said host cell, wherein said method comprises any one of the following steps
   (i) contacting said adenovirus with a ligand which is effective to promote or facilitate said attachment or entry before infecting said host cell; or
   (ii) infecting said host cell by said adenovirus in the presence of said ligand; or
   (iii) contacting said host cell with said ligand and infecting with said adenovirus;
wherein said ligand comprises the amino acid sequence shown in SEQ ID NO: 7.

7. The method of claim 6, wherein said ligand consists of the amino acid sequence as shown in SEQ ID NO: 7.

8. The method of claim 6, wherein said ligand has a dissociation constant (kd) with respect to said adenovirus of 0.01 to 100 nM.

9. The method according to claim 6, wherein said adenovirus is of serotype C.

10. The method according to claim 9, wherein said adenovirus is of serotype 2 or 5.

* * * * *

SEQUENCE LISTING

<160> NUMBER OF SEQ ID NOS: 98

<210> SEQ ID NO 1
<211> LENGTH: 25
<212> TYPE: PRT
<213> ORGANISM: Homo sapiens

<400> SEQUENCE: 1

Leu Arg Ala Tyr Leu Glu Gly Thr Cys Val Glu Trp Leu Arg Arg Tyr
 1               5                  10                  15

Leu Glu Asn Gly Lys Glu Thr Leu Gln
            20                  25

<210> SEQ ID NO 2
<211> LENGTH: 26
<212> TYPE: PRT
<213> ORGANISM: Homo sapiens

<400> SEQUENCE: 2

Asn Ser His Pro Ile Gln Trp Asn Ala Pro Gln Pro Ser His Ile Ser
 1               5                  10                  15

Lys Tyr Ile Leu Arg Trp Arg Pro Lys Asn
            20                  25

```
<210> SEQ ID NO 3
<211> LENGTH: 25
<212> TYPE: PRT
<213> ORGANISM: Homo sapiens

<400> SEQUENCE: 3

Val Lys Val Thr Ile Met Trp Thr Pro Pro Glu Ser Ala Val Thr Gly
1               5                   10                  15

Tyr Arg Val Asp Val Ile Pro Val Asn
            20                  25

<210> SEQ ID NO 4
<211> LENGTH: 25
<212> TYPE: PRT
<213> ORGANISM: Homo sapiens

<400> SEQUENCE: 4

Ser Thr Val Leu Val Arg Trp Thr Pro Pro Arg Ala Gln Ile Thr Gly
1               5                   10                  15

Tyr Arg Leu Thr Val Gly Leu Thr Arg
            20                  25

<210> SEQ ID NO 5
<211> LENGTH: 25
<212> TYPE: PRT
<213> ORGANISM: Homo sapiens

<400> SEQUENCE: 5

Asn Ser Leu Leu Val Ser Trp Gln Pro Pro Arg Ala Arg Ile Thr Gly
1               5                   10                  15

Tyr Ile Ile Lys Tyr Glu Lys Pro Ser
            20                  25

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide MH20

<400> SEQUENCE: 6

Arg Ala Ile Val Gly Phe Arg Val Gln Trp Leu Arg Arg Tyr Phe Val
1               5                   10                  15

Asn Gly Ser Arg
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide FN20

<400> SEQUENCE: 7

Arg His Ile Leu Trp Thr Pro Ala Asn Thr Pro Ala Met Gly Tyr Leu
1               5                   10                  15

Ala Arg Val Ser
            20

<210> SEQ ID NO 8
<211> LENGTH: 18
<212> TYPE: PRT
<213> ORGANISM: Mastadenovirus, serotype 5
```

```
<400> SEQUENCE: 8

Leu Ala Pro Ile Ser Gly Thr Val Gln Ser Ala His Leu Ile Ile Arg
 1               5                  10                  15

Phe Asp

<210> SEQ ID NO 9
<211> LENGTH: 16
<212> TYPE: PRT
<213> ORGANISM: Mastadenovirus, serotype 2

<400> SEQUENCE: 9

Thr Val Ala Ser Val Ser Ile Phe Leu Arg Phe Asp Gln Asn Gly Val
 1               5                  10                  15

<210> SEQ ID NO 10
<211> LENGTH: 14
<212> TYPE: PRT
<213> ORGANISM: Mastadenovirus, serotype 5

<400> SEQUENCE: 10

Leu Asp Pro Glu Tyr Trp Asn Phe Arg Asn Gly Asp Leu Thr
 1               5                  10

<210> SEQ ID NO 11
<211> LENGTH: 13
<212> TYPE: PRT
<213> ORGANISM: Mastadenovirus, serotype 2

<400> SEQUENCE: 11

Asn Ser Ser Leu Lys Lys His Tyr Trp Asn Phe Arg Asn
 1               5                  10

<210> SEQ ID NO 12
<211> LENGTH: 42
<212> TYPE: DNA
<213> ORGANISM: Mastadenovirus, serotype 5

<400> SEQUENCE: 12
cctaaactag gatccggcct tagttttgac agcatgggtg cc                    42

<210> SEQ ID NO 13
<211> LENGTH: 37
<212> TYPE: DNA
<213> ORGANISM: Mastadenovirus, serotype 5

<400> SEQUENCE: 13
ctgtgagttt gattaaggta ccgtgatctg tataagc                          37

<210> SEQ ID NO 14
<211> LENGTH: 36
<212> TYPE: DNA
<213> ORGANISM: Mastadenovirus, serotype 3

<400> SEQUENCE: 14
ggtcttacat ttgactcttc catggctatt gcactg                           36

<210> SEQ ID NO 15
<211> LENGTH: 35
<212> TYPE: DNA
<213> ORGANISM: Mastadenovirus, serotype 3

<400> SEQUENCE: 15
caataaaaaa tgtggtacct tattttgtt gtcag                             35
```

<210> SEQ ID NO 16
<211> LENGTH: 51
<212> TYPE: DNA
<213> ORGANISM: Homo sapiens

<400> SEQUENCE: 16
tcgagaggca tatactttgg actcctgcta atacaccggc aatggggtat g            51

<210> SEQ ID NO 17
<211> LENGTH: 51
<212> TYPE: DNA
<213> ORGANISM: Homo sapiens

<400> SEQUENCE: 17
tcgacatacc ccattgccgg tgtattagca ggagtccaaa gtatatgcct c            51

<210> SEQ ID NO 18
<211> LENGTH: 65
<212> TYPE: DNA
<213> ORGANISM: Homo sapiens

<400> SEQUENCE: 18
tcgagagggc tatagttggg tttagggtgc aatggcttag gcggtatttt gtgaatgggt   60
cgagg                                                              65

<210> SEQ ID NO 19
<211> LENGTH: 65
<212> TYPE: DNA
<213> ORGANISM: Homo sapiens

<400> SEQUENCE: 19
tcgacctcga cccattcaca aaataccgcc taagccattg caccctaaac ccaactatag   60
ccctc                                                              65

<210> SEQ ID NO 20
<211> LENGTH: 30
<212> TYPE: DNA
<213> ORGANISM: Mastadenovirus, serotype 5

<400> SEQUENCE: 20
ccatccgcac ccactatgat cacgttgttg                                    30

<210> SEQ ID NO 21
<211> LENGTH: 27
<212> TYPE: DNA
<213> ORGANISM: Mastadenovirus, serotype 3

<400> SEQUENCE: 21
cttcatttct ttatccccccc atggcca                                      27

<210> SEQ ID NO 22
<211> LENGTH: 35
<212> TYPE: PRT
<213> ORGANISM: Homo sapiens

<400> SEQUENCE: 22

Arg Ala Ile Val Gly Phe Arg Val Gln Trp Leu Arg Arg Tyr Phe Val
 1               5                  10                  15

Asn Gly Ser Arg Lys Met Tyr Pro Arg Gly Asn His Trp Ala Val Gly
                20                  25                  30

```
His Leu Met
         35

<210> SEQ ID NO 23
<211> LENGTH: 35
<212> TYPE: PRT
<213> ORGANISM: Homo sapiens

<400> SEQUENCE: 23

Lys Met Tyr Pro Arg Gly Asn His Trp Ala Val Gly His Leu Met Arg
 1               5                  10                  15

Ala Ile Val Gly Phe Arg Val Gln Trp Leu Arg Arg Tyr Phe Val Asn
             20                  25                  30

Gly Ser Arg
         35

<210> SEQ ID NO 24
<211> LENGTH: 10
<212> TYPE: PRT
<213> ORGANISM: Artificial Sequence
<220> FEATURE:
<223> OTHER INFORMATION: Gastrin Releasing Peptide (GRP)

<400> SEQUENCE: 24

Gly Asn His Trp Ala Val Gly His Leu Met
 1               5                  10

<210> SEQ ID NO 25
<211> LENGTH: 6
<212> TYPE: PRT
<213> ORGANISM: Artificial Sequence
<220> FEATURE:
<223> OTHER INFORMATION: Phagotope

<400> SEQUENCE: 25

Gly Ile Ser His Thr Gly
 1               5

<210> SEQ ID NO 26
<211> LENGTH: 6
<212> TYPE: PRT
<213> ORGANISM: Artificial Sequence
<220> FEATURE:
<223> OTHER INFORMATION: Phagotope

<400> SEQUENCE: 26

Gly Ala Ser His Thr Val
 1               5

<210> SEQ ID NO 27
<211> LENGTH: 6
<212> TYPE: PRT
<213> ORGANISM: Artificial Sequence
<220> FEATURE:
<223> OTHER INFORMATION: Phagotope

<400> SEQUENCE: 27

Gln Ser Ala His Leu Ile
 1               5

<210> SEQ ID NO 28
<211> LENGTH: 5
<212> TYPE: PRT
<213> ORGANISM: Artificial Sequence
<220> FEATURE:
<223> OTHER INFORMATION: Phagotope
```

```
<400> SEQUENCE: 28

Leu Ala Pro Ile Ser
 1               5

<210> SEQ ID NO 29
<211> LENGTH: 4
<212> TYPE: PRT
<213> ORGANISM: Artificial Sequence
<220> FEATURE:
<223> OTHER INFORMATION: Phagotope

<400> SEQUENCE: 29

Val Ala Pro Ser
 1

<210> SEQ ID NO 30
<211> LENGTH: 6
<212> TYPE: PRT
<213> ORGANISM: Artificial Sequence
<220> FEATURE:
<223> OTHER INFORMATION: Phagotope

<400> SEQUENCE: 30

Leu Ile Pro Phe Asn Ser
 1               5

<210> SEQ ID NO 31
<211> LENGTH: 4
<212> TYPE: PRT
<213> ORGANISM: Artificial Sequence
<220> FEATURE:
<223> OTHER INFORMATION: Phagotope

<400> SEQUENCE: 31

Tyr Trp Asn Phe
 1

<210> SEQ ID NO 32
<211> LENGTH: 6
<212> TYPE: PRT
<213> ORGANISM: Artificial Sequence
<220> FEATURE:
<223> OTHER INFORMATION: Phagotope

<400> SEQUENCE: 32

Phe Trp Leu Ala Val Arg
 1               5

<210> SEQ ID NO 33
<211> LENGTH: 6
<212> TYPE: PRT
<213> ORGANISM: Artificial Sequence
<220> FEATURE:
<223> OTHER INFORMATION: Phagotope

<400> SEQUENCE: 33

Trp Ala Leu Phe Arg Ser
 1               5

<210> SEQ ID NO 34
<211> LENGTH: 5
<212> TYPE: PRT
<213> ORGANISM: Artificial Sequence
<220> FEATURE:
<223> OTHER INFORMATION: Phagotope
```

```
<400> SEQUENCE: 34

Tyr Trp Asn Phe Arg
 1               5

<210> SEQ ID NO 35
<211> LENGTH: 28
<212> TYPE: PRT
<213> ORGANISM: Artificial Sequence
<220> FEATURE:
<223> OTHER INFORMATION: Phagotope

<400> SEQUENCE: 35

Val Leu Ala Val Lys Gly Ser Leu Ala Pro Ile Ser Gly Thr Val Gln
 1               5                  10                  15

Ser Ala His Leu Ile Ile Arg Phe Asp Glu Asn Gly
                20                  25

<210> SEQ ID NO 36
<211> LENGTH: 6
<212> TYPE: PRT
<213> ORGANISM: Artificial Sequence
<220> FEATURE:
<223> OTHER INFORMATION: Phagotope

<400> SEQUENCE: 36

Val Phe Val Lys Leu Pro
 1               5

<210> SEQ ID NO 37
<211> LENGTH: 6
<212> TYPE: PRT
<213> ORGANISM: Artificial Sequence
<220> FEATURE:
<223> OTHER INFORMATION: Phagotope

<400> SEQUENCE: 37

Pro Asp Val Ala Pro Ser
 1               5

<210> SEQ ID NO 38
<211> LENGTH: 6
<212> TYPE: PRT
<213> ORGANISM: Artificial Sequence
<220> FEATURE:
<223> OTHER INFORMATION: Phagotope

<400> SEQUENCE: 38

Leu Ile Pro Phe Asn Ser
 1               5

<210> SEQ ID NO 39
<211> LENGTH: 6
<212> TYPE: PRT
<213> ORGANISM: Artificial Sequence
<220> FEATURE:
<223> OTHER INFORMATION: Phagotope

<400> SEQUENCE: 39

Leu Ser Asn Gln Ser Gly
 1               5

<210> SEQ ID NO 40
<211> LENGTH: 6
<212> TYPE: PRT
<213> ORGANISM: Artificial Sequence
<220> FEATURE:
```

```
<223> OTHER INFORMATION: Phagotope

<400> SEQUENCE: 40

Ser Gly Val Gly Gln Ala
 1               5

<210> SEQ ID NO 41
<211> LENGTH: 6
<212> TYPE: PRT
<213> ORGANISM: Artificial Sequence
<220> FEATURE:
<223> OTHER INFORMATION: Phagotope

<400> SEQUENCE: 41

Ser Val Gly Asp Tyr Gly
 1               5

<210> SEQ ID NO 42
<211> LENGTH: 6
<212> TYPE: PRT
<213> ORGANISM: Artificial Sequence
<220> FEATURE:
<223> OTHER INFORMATION: Phagotope

<400> SEQUENCE: 42

Gly Ile Ser His Thr Gly
 1               5

<210> SEQ ID NO 43
<211> LENGTH: 6
<212> TYPE: PRT
<213> ORGANISM: Artificial Sequence
<220> FEATURE:
<223> OTHER INFORMATION: Phagotope

<400> SEQUENCE: 43

Gly Ala Ser His Thr Val
 1               5

<210> SEQ ID NO 44
<211> LENGTH: 6
<212> TYPE: PRT
<213> ORGANISM: Artificial Sequence
<220> FEATURE:
<223> OTHER INFORMATION: Phagotope

<400> SEQUENCE: 44

His Gly Gln Tyr Arg Met
 1               5

<210> SEQ ID NO 45
<211> LENGTH: 6
<212> TYPE: PRT
<213> ORGANISM: Artificial Sequence
<220> FEATURE:
<223> OTHER INFORMATION: Phagotope

<400> SEQUENCE: 45

Arg Arg Ile Phe Arg Asp
 1               5

<210> SEQ ID NO 46
<211> LENGTH: 17
<212> TYPE: PRT
<213> ORGANISM: Artificial Sequence
<220> FEATURE:
<223> OTHER INFORMATION: Phagotope
```

```
<400> SEQUENCE: 46

Asn Ser Phe Leu Asp Pro Glu Tyr Trp Asn Phe Arg Asn Gly Asp Leu
1               5                   10                  15
Thr

<210> SEQ ID NO 47
<211> LENGTH: 6
<212> TYPE: PRT
<213> ORGANISM: Artificial Sequence
<220> FEATURE:
<223> OTHER INFORMATION: Phagotope

<400> SEQUENCE: 47

Met Gln Pro Val Tyr Phe
1               5

<210> SEQ ID NO 48
<211> LENGTH: 6
<212> TYPE: PRT
<213> ORGANISM: Artificial Sequence
<220> FEATURE:
<223> OTHER INFORMATION: Phagotope

<400> SEQUENCE: 48

Leu Gly Pro Val Asn Ser
1               5

<210> SEQ ID NO 49
<211> LENGTH: 6
<212> TYPE: PRT
<213> ORGANISM: Artificial Sequence
<220> FEATURE:
<223> OTHER INFORMATION: Phagotope

<400> SEQUENCE: 49

Ala Leu Pro His Ile Val
1               5

<210> SEQ ID NO 50
<211> LENGTH: 6
<212> TYPE: PRT
<213> ORGANISM: Artificial Sequence
<220> FEATURE:
<223> OTHER INFORMATION: Phagotope

<400> SEQUENCE: 50

Ala Pro His Glu Leu Arg
1               5

<210> SEQ ID NO 51
<211> LENGTH: 6
<212> TYPE: PRT
<213> ORGANISM: Artificial Sequence
<220> FEATURE:
<223> OTHER INFORMATION: Phagotope

<400> SEQUENCE: 51

Met Asn Val Gly Ala His
1               5

<210> SEQ ID NO 52
<211> LENGTH: 6
<212> TYPE: PRT
<213> ORGANISM: Artificial Sequence
<220> FEATURE:
```

```
<223> OTHER INFORMATION: Phagotope

<400> SEQUENCE: 52

Val Thr Ser Thr Tyr His
 1               5

<210> SEQ ID NO 53
<211> LENGTH: 6
<212> TYPE: PRT
<213> ORGANISM: Artificial Sequence
<220> FEATURE:
<223> OTHER INFORMATION: Phagotope

<400> SEQUENCE: 53

Leu Gln Lys Val His Arg
 1               5

<210> SEQ ID NO 54
<211> LENGTH: 6
<212> TYPE: PRT
<213> ORGANISM: Artificial Sequence
<220> FEATURE:
<223> OTHER INFORMATION: Phagotope

<400> SEQUENCE: 54

Asp Leu Trp Ser Val Leu
 1               5

<210> SEQ ID NO 55
<211> LENGTH: 6
<212> TYPE: PRT
<213> ORGANISM: Artificial Sequence
<220> FEATURE:
<223> OTHER INFORMATION: Phagotope

<400> SEQUENCE: 55

Phe Trp Leu Ala Val Arg
 1               5

<210> SEQ ID NO 56
<211> LENGTH: 6
<212> TYPE: PRT
<213> ORGANISM: Artificial Sequence
<220> FEATURE:
<223> OTHER INFORMATION: Phagotope

<400> SEQUENCE: 56

Trp Ala Leu Phe Arg Ser
 1               5

<210> SEQ ID NO 57
<211> LENGTH: 6
<212> TYPE: PRT
<213> ORGANISM: Artificial Sequence
<220> FEATURE:
<223> OTHER INFORMATION: Phagotope

<400> SEQUENCE: 57

Tyr Leu Gly Phe Phe Lys
 1               5

<210> SEQ ID NO 58
<211> LENGTH: 6
<212> TYPE: PRT
<213> ORGANISM: Artificial Sequence
<220> FEATURE:
<223> OTHER INFORMATION: Phagotope
```

```
<400> SEQUENCE: 58

Ile Ala Arg Leu Ile Ser
 1               5

<210> SEQ ID NO 59
<211> LENGTH: 6
<212> TYPE: PRT
<213> ORGANISM: Artificial Sequence
<220> FEATURE:
<223> OTHER INFORMATION: Phagotope

<400> SEQUENCE: 59

Arg Asn Tyr Thr Leu Thr
 1               5

<210> SEQ ID NO 60
<211> LENGTH: 6
<212> TYPE: PRT
<213> ORGANISM: Artificial Sequence
<220> FEATURE:
<223> OTHER INFORMATION: Phagotope

<400> SEQUENCE: 60

Arg Asp Ala Val Met Ile
 1               5

<210> SEQ ID NO 61
<211> LENGTH: 6
<212> TYPE: PRT
<213> ORGANISM: Artificial Sequence
<220> FEATURE:
<223> OTHER INFORMATION: Phagotope

<400> SEQUENCE: 61

Ser Arg Pro Thr Met Leu
 1               5

<210> SEQ ID NO 62
<211> LENGTH: 6
<212> TYPE: PRT
<213> ORGANISM: Artificial Sequence
<220> FEATURE:
<223> OTHER INFORMATION: Phagotope

<400> SEQUENCE: 62

Arg His Arg Met Leu Gln
 1               5

<210> SEQ ID NO 63
<211> LENGTH: 6
<212> TYPE: PRT
<213> ORGANISM: Artificial Sequence
<220> FEATURE:
<223> OTHER INFORMATION: Phagotope

<400> SEQUENCE: 63

Arg Arg His Trp Pro Phe
 1               5

<210> SEQ ID NO 64
<211> LENGTH: 6
<212> TYPE: PRT
<213> ORGANISM: Artificial Sequence
<220> FEATURE:
<223> OTHER INFORMATION: Phagotope
```

```
<400> SEQUENCE: 64

Trp Tyr Glu Trp Ile Gly
 1               5

<210> SEQ ID NO 65
<211> LENGTH: 6
<212> TYPE: PRT
<213> ORGANISM: Artificial Sequence
<220> FEATURE:
<223> OTHER INFORMATION: Phagotope

<400> SEQUENCE: 65

Trp Val Ile Trp Ser Ile
 1               5

<210> SEQ ID NO 66
<211> LENGTH: 6
<212> TYPE: PRT
<213> ORGANISM: Artificial Sequence
<220> FEATURE:
<223> OTHER INFORMATION: Phagotope

<400> SEQUENCE: 66

Ile Leu Trp Thr Pro Gly
 1               5

<210> SEQ ID NO 67
<211> LENGTH: 6
<212> TYPE: PRT
<213> ORGANISM: Artificial Sequence
<220> FEATURE:
<223> OTHER INFORMATION: Phagotope

<400> SEQUENCE: 67

Leu Gln Tyr Ser Leu Pro
 1               5

<210> SEQ ID NO 68
<211> LENGTH: 6
<212> TYPE: PRT
<213> ORGANISM: Artificial Sequence
<220> FEATURE:
<223> OTHER INFORMATION: Phagotope

<400> SEQUENCE: 68

Leu Leu Asp Phe Pro Ala
 1               5

<210> SEQ ID NO 69
<211> LENGTH: 6
<212> TYPE: PRT
<213> ORGANISM: Artificial Sequence
<220> FEATURE:
<223> OTHER INFORMATION: Phagotope

<400> SEQUENCE: 69

Leu Thr Pro Asn Thr Ile
 1               5

<210> SEQ ID NO 70
<211> LENGTH: 6
<212> TYPE: PRT
<213> ORGANISM: Artificial Sequence
<220> FEATURE:
<223> OTHER INFORMATION: Phagotope

<400> SEQUENCE: 70
```

```
Leu Gly Lys Ala Leu Pro
1               5
```

<210> SEQ ID NO 71
<211> LENGTH: 6
<212> TYPE: PRT
<213> ORGANISM: Artificial Sequence
<220> FEATURE:
<223> OTHER INFORMATION: Phagotope

<400> SEQUENCE: 71

```
Ser Pro His Gly Ser Gly
1               5
```

<210> SEQ ID NO 72
<211> LENGTH: 6
<212> TYPE: PRT
<213> ORGANISM: Artificial Sequence
<220> FEATURE:
<223> OTHER INFORMATION: Phagotope

<400> SEQUENCE: 72

```
Ala Pro Met Val Ala Leu
1               5
```

<210> SEQ ID NO 73
<211> LENGTH: 6
<212> TYPE: PRT
<213> ORGANISM: Artificial Sequence
<220> FEATURE:
<223> OTHER INFORMATION: Phagotope

<400> SEQUENCE: 73

```
Thr Ala Ala Met Tyr Arg
1               5
```

<210> SEQ ID NO 74
<211> LENGTH: 6
<212> TYPE: PRT
<213> ORGANISM: Artificial Sequence
<220> FEATURE:
<223> OTHER INFORMATION: Phagotope

<400> SEQUENCE: 74

```
Leu Phe Ile Ala Arg Leu
1               5
```

<210> SEQ ID NO 75
<211> LENGTH: 6
<212> TYPE: PRT
<213> ORGANISM: Artificial Sequence
<220> FEATURE:
<223> OTHER INFORMATION: Phagotope

<400> SEQUENCE: 75

```
Tyr Leu Tyr Gly Arg Val
1               5
```

<210> SEQ ID NO 76
<211> LENGTH: 6
<212> TYPE: PRT
<213> ORGANISM: Artificial Sequence
<220> FEATURE:
<223> OTHER INFORMATION: Phagotope

<400> SEQUENCE: 76

```
Ala Arg Val Ser Arg Ser
  1               5

<210> SEQ ID NO 77
<211> LENGTH: 20
<212> TYPE: PRT
<213> ORGANISM: Artificial Sequence
<220> FEATURE:
<223> OTHER INFORMATION: Phagotope

<400> SEQUENCE: 77

Arg His Ile Leu Trp Thr Pro Ala Asn Thr Pro Ala Met Gly Tyr Leu
  1               5                  10                  15

Ala Arg Val Ser
             20

<210> SEQ ID NO 78
<211> LENGTH: 26
<212> TYPE: PRT
<213> ORGANISM: Artificial Sequence
<220> FEATURE:
<223> OTHER INFORMATION: Phagotope

<400> SEQUENCE: 78

Asn Ser His Pro Ile Gln Trp Asn Ala Pro Gln Pro Ser His Ile Ser
  1               5                  10                  15

Lys Tyr Ile Leu Arg Trp Arg Pro Lys Asn
             20                  25

<210> SEQ ID NO 79
<211> LENGTH: 25
<212> TYPE: PRT
<213> ORGANISM: Artificial Sequence
<220> FEATURE:
<223> OTHER INFORMATION: Phagotope

<400> SEQUENCE: 79

Val Lys Val Thr Ile Met Trp Thr Pro Pro Glu Ser Ala Val Thr Gly
  1               5                  10                  15

Tyr Arg Val Asp Val Ile Pro Val Asn
             20                  25

<210> SEQ ID NO 80
<211> LENGTH: 25
<212> TYPE: PRT
<213> ORGANISM: Artificial Sequence
<220> FEATURE:
<223> OTHER INFORMATION: Phagotope

<400> SEQUENCE: 80

Ser Thr Val Leu Val Arg Trp Thr Pro Pro Arg Ala Gln Ile Thr Gly
  1               5                  10                  15

Tyr Arg Leu Thr Val Gly Leu Thr Arg
             20                  25

<210> SEQ ID NO 81
<211> LENGTH: 25
<212> TYPE: PRT
<213> ORGANISM: Artificial Sequence
<220> FEATURE:
<223> OTHER INFORMATION: Phagotope

<400> SEQUENCE: 81

Asn Ser Leu Leu Val Ser Trp Gln Pro Pro Arg Ala Arg Ile Thr Gly
  1               5                  10                  15
```

Tyr Ile Ile Lys Tyr Glu Lys Pro Ser
            20                  25

<210> SEQ ID NO 82
<211> LENGTH: 6
<212> TYPE: PRT
<213> ORGANISM: Artificial Sequence
<220> FEATURE:
<223> OTHER INFORMATION: Phagotope

<400> SEQUENCE: 82

Ala Arg Ala Ile Val Gly
1               5

<210> SEQ ID NO 83
<211> LENGTH: 6
<212> TYPE: PRT
<213> ORGANISM: Artificial Sequence
<220> FEATURE:
<223> OTHER INFORMATION: Phagotope

<400> SEQUENCE: 83

Phe Val Trp Gly Leu Ser
1               5

<210> SEQ ID NO 84
<211> LENGTH: 6
<212> TYPE: PRT
<213> ORGANISM: Artificial Sequence
<220> FEATURE:
<223> OTHER INFORMATION: Phagotope

<400> SEQUENCE: 84

Phe Arg Val Gln Trp Leu
1               5

<210> SEQ ID NO 85
<211> LENGTH: 6
<212> TYPE: PRT
<213> ORGANISM: Artificial Sequence
<220> FEATURE:
<223> OTHER INFORMATION: Phagotope

<400> SEQUENCE: 85

Gln Val His Leu Phe Arg
1               5

<210> SEQ ID NO 86
<211> LENGTH: 6
<212> TYPE: PRT
<213> ORGANISM: Artificial Sequence
<220> FEATURE:
<223> OTHER INFORMATION: Phagotope

<400> SEQUENCE: 86

Val Gln Trp Phe Lys Pro
1               5

<210> SEQ ID NO 87
<211> LENGTH: 6
<212> TYPE: PRT
<213> ORGANISM: Artificial Sequence
<220> FEATURE:
<223> OTHER INFORMATION: Phagotope

<400> SEQUENCE: 87

```
Trp Ile Phe Leu Met Gln
 1               5

<210> SEQ ID NO 88
<211> LENGTH: 6
<212> TYPE: PRT
<213> ORGANISM: Artificial Sequence
<220> FEATURE:
<223> OTHER INFORMATION: Phagotope

<400> SEQUENCE: 88

Arg Arg Tyr Phe Val Asn
 1               5

<210> SEQ ID NO 89
<211> LENGTH: 6
<212> TYPE: PRT
<213> ORGANISM: Artificial Sequence
<220> FEATURE:
<223> OTHER INFORMATION: Phagotope

<400> SEQUENCE: 89

Tyr Phe Gly Ser Asn Ser
 1               5

<210> SEQ ID NO 90
<211> LENGTH: 6
<212> TYPE: PRT
<213> ORGANISM: Artificial Sequence
<220> FEATURE:
<223> OTHER INFORMATION: Phagotope

<400> SEQUENCE: 90

Ala Tyr Gly Val Met Pro
 1               5

<210> SEQ ID NO 91
<211> LENGTH: 6
<212> TYPE: PRT
<213> ORGANISM: Artificial Sequence
<220> FEATURE:
<223> OTHER INFORMATION: Phagotope

<400> SEQUENCE: 91

Leu Ala Pro Leu Gly Lys
 1               5

<210> SEQ ID NO 92
<211> LENGTH: 6
<212> TYPE: PRT
<213> ORGANISM: Artificial Sequence
<220> FEATURE:
<223> OTHER INFORMATION: Phagotope

<400> SEQUENCE: 92

Ser Arg Leu Lys Met Gly
 1               5

<210> SEQ ID NO 93
<211> LENGTH: 6
<212> TYPE: PRT
<213> ORGANISM: Artificial Sequence
<220> FEATURE:
<223> OTHER INFORMATION: Phagotope

<400> SEQUENCE: 93

His Met Glu Leu Leu Met
```

```
<210> SEQ ID NO 94
<211> LENGTH: 6
<212> TYPE: PRT
<213> ORGANISM: Artificial Sequence
<220> FEATURE:
<223> OTHER INFORMATION: Phagotope

<400> SEQUENCE: 94

His Ser Asn Gly Ser Arg
 1               5

<210> SEQ ID NO 95
<211> LENGTH: 6
<212> TYPE: PRT
<213> ORGANISM: Artificial Sequence
<220> FEATURE:
<223> OTHER INFORMATION: Phagotope

<400> SEQUENCE: 95

Thr Arg Val Arg Thr Ser
 1               5

<210> SEQ ID NO 96
<211> LENGTH: 6
<212> TYPE: PRT
<213> ORGANISM: Artificial Sequence
<220> FEATURE:
<223> OTHER INFORMATION: Phagotope

<400> SEQUENCE: 96

Arg Ser Glu Glu Thr Ile
 1               5

<210> SEQ ID NO 97
<211> LENGTH: 24
<212> TYPE: PRT
<213> ORGANISM: Artificial Sequence
<220> FEATURE:
<223> OTHER INFORMATION: Phagotope

<400> SEQUENCE: 97

Ala Arg Ala Ile Val Gly Phe Arg Val Gln Trp Leu Arg Arg Tyr Phe
 1               5                  10                  15

Val Asn Gly Ser Arg Glu Thr Ile
             20

<210> SEQ ID NO 98
<211> LENGTH: 25
<212> TYPE: PRT
<213> ORGANISM: Artificial Sequence
<220> FEATURE:
<223> OTHER INFORMATION: Phagotope

<400> SEQUENCE: 98

Leu Arg Ala Tyr Leu Glu Gly Thr Cys Val Glu Trp Leu Arg Arg Tyr
 1               5                  10                  15

Leu Glu Asn Gly Lys Glu Thr Leu Gln
             20                  25
```